US009395721B2

(12) United States Patent
Perkins et al.

(10) Patent No.: US 9,395,721 B2
(45) Date of Patent: Jul. 19, 2016

(54) IN-SITU MONITORING OF FABRICATION OF INTEGRATED COMPUTATIONAL ELEMENTS

(71) Applicant: Halliburton Energy Services, Inc., Houston, TX (US)

(72) Inventors: David L. Perkins, The Woodlands, TX (US); Robert Paul Freese, Pittsboro, NC (US); Christopher Michael Jones, Houston, TX (US); Richard Neal Gardner, Raleigh, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/397,818

(22) PCT Filed: Dec. 24, 2013

(86) PCT No.: PCT/US2013/077690
§ 371 (c)(1),
(2) Date: Oct. 29, 2014

(87) PCT Pub. No.: WO2015/099711
PCT Pub. Date: Jul. 2, 2015

(65) Prior Publication Data
US 2016/0018818 A1    Jan. 21, 2016

(51) Int. Cl.
*G01N 37/00* (2006.01)
*G05B 19/418* (2006.01)
(Continued)

(52) U.S. Cl.
CPC .......... *G05B 19/41875* (2013.01); *C23C 14/30* (2013.01); *C23C 14/547* (2013.01);
(Continued)

(58) Field of Classification Search
CPC . G05B 19/41875; G01N 21/25; C23C 14/547
USPC .......................................................... 702/83
See application file for complete search history.

(56) References Cited

U.S. PATENT DOCUMENTS 5,075,550 A    12/1991 Miller et al.
5,399,229 A    3/1995 Stefani et al.
(Continued)

FOREIGN PATENT DOCUMENTS

WO    2004/015364    2/2004
WO    2006/031733    3/2006
(Continued)

OTHER PUBLICATIONS

Authorized Officer Lee, Hun Gil in International Search Report and Written Opinion in International Application No. PCT/US2014/016603, mailed Nov. 13, 2014, 9 pages.
(Continued)

*Primary Examiner* — Mischita Henson
*Assistant Examiner* — Stephanie Bloss
(74) *Attorney, Agent, or Firm* — Benjamin Fite; Fish & Richardson P.C.

(57) ABSTRACT

Techniques include receiving a design of an integrated computational element (ICE), the ICE design including specification of a substrate and a plurality of layers, their respective target thicknesses and complex refractive indices, complex refractive indices of adjacent layers being different from each other, and a notional ICE fabricated in accordance with the ICE design being related to a characteristic of a sample; forming at least some of the plurality of layers of the ICE in accordance with the ICE design; performing at least two different types of in-situ measurements; predicting, using results of the at least two different types of in situ measurements, performance of the ICE relative to the ICE design; and adjusting the forming of the layers remaining to be formed, at least in part, by updating the ICE design based on the predicted performance.

61 Claims, 6 Drawing Sheets

(51) Int. Cl.
  *G01B 11/06* (2006.01)
  *G01N 21/84* (2006.01)
  *G01N 21/21* (2006.01)
  *C23C 14/30* (2006.01)
  *C23C 14/54* (2006.01)
  *G01N 21/25* (2006.01)
  *H01J 27/02* (2006.01)
  *H01J 27/08* (2006.01)
  *H01J 37/34* (2006.01)

(52) U.S. Cl.
  CPC ........ *G01B11/0625* (2013.01); *G01B 11/0683* (2013.01); *G01N 21/211* (2013.01); *G01N 21/25* (2013.01); *G01N 21/8422* (2013.01); *H01J 27/022* (2013.01); *H01J 27/08* (2013.01); *H01J 37/3488* (2013.01); *G01N 2021/213* (2013.01); *G05B 2219/32368* (2013.01)

(56) References Cited

U.S. PATENT DOCUMENTS

| | | |
|---|---|---|
| 5,453,716 A | 9/1995 | Person et al. |
| 5,537,479 A | 7/1996 | Kreisel et al. |
| 5,619,366 A | 4/1997 | Rhoads et al. |
| 6,078,389 A | 6/2000 | Zetter |
| 6,154,550 A | 11/2000 | Beyer |
| 6,163,259 A | 12/2000 | Barsumian et al. |
| 6,198,531 B1 | 3/2001 | Myrick et al. |
| 6,213,250 B1 | 4/2001 | Wisniewski et al. |
| 6,217,720 B1* | 4/2001 | Sullivan ............... C23C 14/548 204/192.13 |
| 6,529,276 B1 | 3/2003 | Myrick |
| 6,646,753 B2 | 11/2003 | Zhang et al. |
| 6,777,684 B1 | 8/2004 | Volkov et al. |
| 6,804,060 B1 | 10/2004 | Tsai et al. |
| 6,905,578 B1 | 6/2005 | Moslehi et al. |
| 6,965,431 B2 | 11/2005 | Vo-Dinh et al. |
| 7,138,156 B1* | 11/2006 | Myrick ............... G02B 5/285 359/359 |
| 7,163,901 B2 | 1/2007 | Downey |
| 7,332,044 B2 | 2/2008 | Sidorin et al. |
| 7,679,563 B2 | 3/2010 | Werner et al. |
| 7,697,141 B2 | 4/2010 | Jones et al. |
| 7,753,847 B2 | 7/2010 | Greenleaf et al. |
| 7,777,870 B2 | 8/2010 | Hayes et al. |
| 7,792,644 B2 | 9/2010 | Kotter et al. |
| 7,828,929 B2 | 11/2010 | Lee et al. |
| 7,911,605 B2 | 3/2011 | Myrick et al. |
| 7,920,258 B2 | 4/2011 | Myrick et al. |
| 8,054,212 B1 | 11/2011 | Holly et al. |
| 8,106,850 B1 | 1/2012 | Gregoire et al. |
| 8,164,061 B2 | 4/2012 | Pawlak et al. |
| 8,216,161 B2 | 7/2012 | Darlington et al. |
| 8,252,112 B2 | 8/2012 | Ovshinsky |
| 2002/0090650 A1 | 7/2002 | Empedocles et al. |
| 2005/0054928 A1 | 3/2005 | Cerofolini |
| 2006/0142955 A1* | 6/2006 | Jones ............... E21B 47/102 702/32 |
| 2008/0212168 A1 | 9/2008 | Olmstead et al. |
| 2009/0182693 A1 | 7/2009 | Fulton et al. |
| 2009/0213381 A1 | 8/2009 | Appel et al. |
| 2010/0004773 A1* | 1/2010 | Kochergin ............ G01N 21/211 700/103 |
| 2010/0089906 A1 | 4/2010 | Plantamura |
| 2010/0153048 A1 | 6/2010 | Myrick et al. |
| 2010/0245096 A1 | 9/2010 | Jones et al. |
| 2010/0245819 A1* | 9/2010 | Li ............... G01B 11/0641 356/327 |
| 2012/0150451 A1 | 6/2012 | Skinner et al. |
| 2012/0268744 A1 | 10/2012 | Wolf et al. |
| 2013/0032338 A1 | 2/2013 | Kalia et al. |
| 2013/0035262 A1 | 2/2013 | Freese et al. |
| 2013/0083320 A1* | 4/2013 | Gao ............... G01N 21/9501 356/237.5 |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2013/0287061 A1 | 10/2013 | Freese et al. |
| 2013/0323484 A1 | 12/2013 | Pelletier et al. |

FOREIGN PATENT DOCUMENTS

| | | |
|---|---|---|
| WO | 2007/015115 | 2/2007 |
| WO | 2011/103066 | 8/2011 |
| WO | 2013/022556 | 2/2013 |

OTHER PUBLICATIONS

Extended European Search Report, European Application No. EP13884957.5, Jun. 17, 2015, 7 pages.
Soyemi et al. "Design and Testing of a Multivariate Optical Element: The First Demonstration of Multivariate Optical Computing for Predictive Spectroscopy", Analytical Chemistry, American Chemical Society, XP001063566, Mar. 15, 2001, pp. 1069-1079.
International Search Report and Written Opinion of the International Searching Authority issued in International Application No. PCT/US2013/077690 on Sep. 22, 2014; 10 pages.
International Search Report and Written Opinion of the International Searching Authority issued in International Application No. PCT/US2013/077686 on Sep. 24, 2014; 14 pages.
International Search Report and Written Opinion of the International Searching Authority issued in International Application No. PCT/US2013/077688 on Sep. 25, 2014; 11 pages.
International Search Report and Written Opinion of the International Searching Authority issued in International Application No. PCT/US2013/077687 on Sep. 23, 2014; 11 pages.
Frey et al., "Temperature-dependent refractive index of silicon and germanium," NASA Goodard Space Flight Center, Greenbelt, MD, 2006, 10 pages.
Morton et al., "Optical Monitoring of Thin-films Using Spectroscopic Ellipsometry," Society of Vacuum Coaters, 45th Annual Technical Conference Proceedings, 2002, 7 pages.
Eastwood et al., "Field applications of stand-off sensing using visible/NIR multivariate optical computing," Department of Chemistry and Biochemistry, University of South Carolina, SPE vol. 4199, 2001, 10 pages.
Paul et al., "Fabrication of mid-infrared frequency-selective surfaces by soft lithography", Applied Optics, v. 40, No. 25, Sep. 2001, 5 pages.
Haibach et al., "Precision in multivariate optical computing," Applied Optics, vol. 43, No. 10, Apr. 1, 2004, 11 pages.
J.A. Woollam Co., Inc., Characterizing Processes with Ease® In Situ Applications, Application Note, 2009, 3 pages.
Li, "Refractive Index of Silicon and Germanium and Its Wavelength and Temperature Derivatives," Center for Information and Numerical Data Analysis and Synthesis, Purdue University, J. Phys. Chem. Ref. Data, vol. 9, No. 3, 1980, 98 pages.
Myrick, "Multivariate optical elements simplify spectroscopy," Laser Focus World, Mar. 1, 2002, access date Feb. 28, 2013, 3 pages http://www.laserfocusworld.com/articles/print/volume-38/issue-3/features/spectroscopy/multivariate-optical-elements-simplify-spectroscopy.html.
Myrick et al., "A single-element all-optical approach to chemometric prediction," Vibrational Spectroscopy 28, 2002, 9 pages.
Myrick et al., "Spectral tolerance determination for multivariate optical element design," Fresenius J Anal Chem, 369, 2001, 5 pages.
Myrick et al., "Application of multivariate optical computing to simple near-infrared point measurements," SPIE vol. 4574, Department of Chemistry and biochemistry, University of South Carolina, 2002, 8 pages.

(56) References Cited

OTHER PUBLICATIONS

Rabady et al., "High-resolution photometric optical monitoring for thin-film deposition," Applied Optics, Optical Society of America, vol. 43, No. 1, Jan. 1, 2004, 6 pages.

Priore et al., "Novel Imaging Systems: Multivariate Optical Computing in the UV-VIS," Department of Chemistry and Biochemistry, University of South Carolina, 2003, 5 pages.

Grader et al., "Fourier transform infrared spectroscopy of a single aerosol particle," J. Chem. Phys. 86 (11), Jun. 1, 1987, 7 pages.

Soyemi et al., "Novel Filter Design Algorithm for Multivariate Optical Computing," Advanced Environmental and Chemical Sensing Technology, SPIE vol. 4205, 2001, 12 pages.

Telemark, "Model 820 In-Situ Spectroscopic Optical Monitor," Dec. 2010, 4 pages.

Bossard et al., "The Design and fabrication of planar multiband metallodielectric frequency selective surfaces for infrared applications", IEEE Trans. on Antennas and Propagation, v. 50, No. 4, Apr. 2006, 12 pages.

Woollam et al., "Overview of Variable Angle Spectroscopic Ellipsometer (VASE), Part 1: Basic Theory and Typical Applications," Society of Photo-Optical Instrumentation Engineers, Critical Reviews of Optical Science Technology CR72, 1999, 28 pages.

Zoeller et al., "Substantial progress in optical monitoring by intermittent measurement technique," SPIE, Published in the processing of the OSD, Jena 2005, vol. 5963-13, 9 pages.

Sullivan et al., "Manufacture of Complex Optical Multilayer Filters using an Automated Deposition System", XP002951089, vol. 51, No. 4, Published in 1998, pp. 647-654.

Haibach et al., "On-Line Reoptimization of Filter Designs for Multivariate Optical Elements", Applied Optics, Optical Society of America, XP001152469, vol. 42, No. 10, Apr. 1, 2003, pp. 1833-1838.

\* cited by examiner

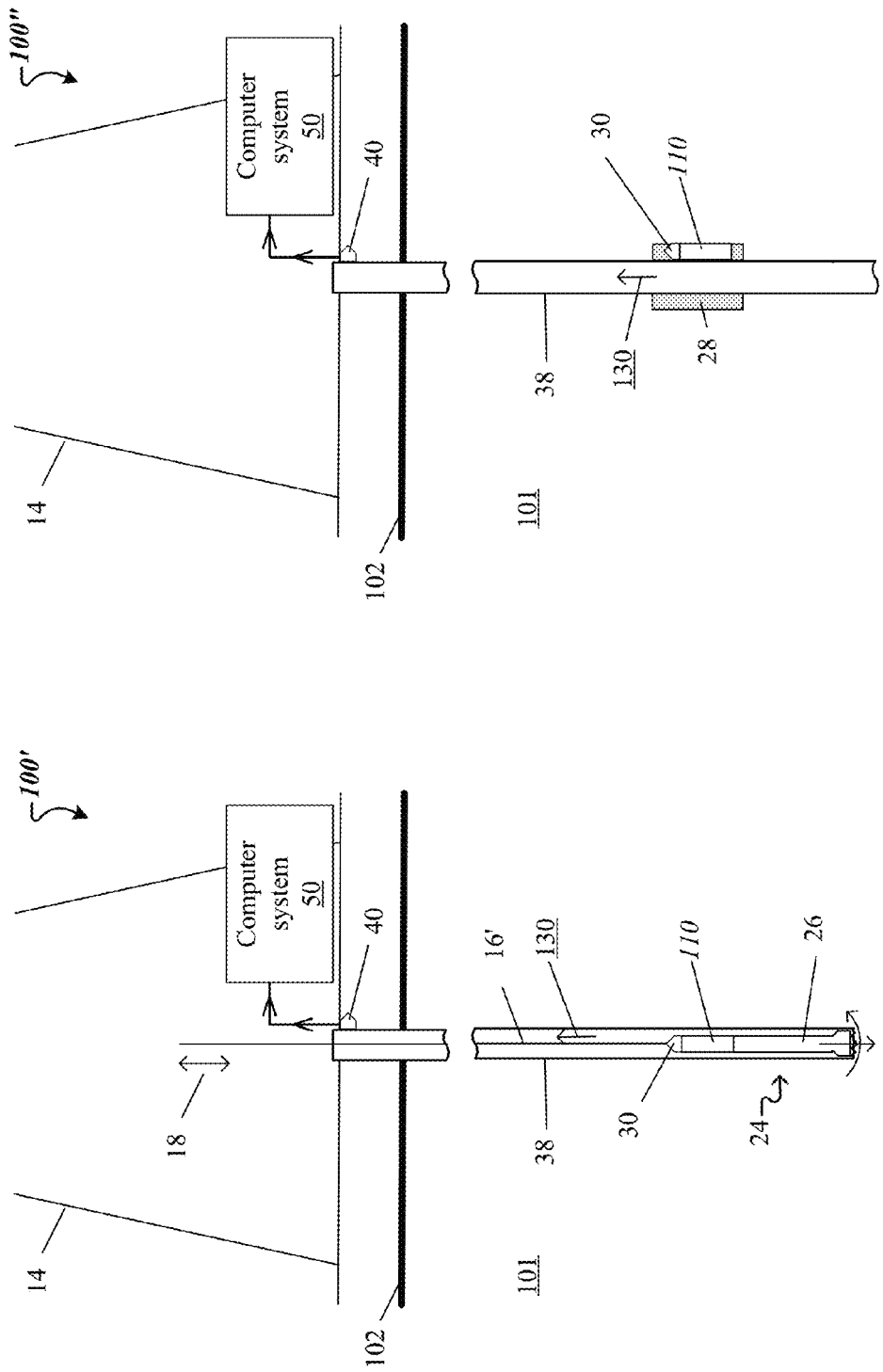

IN-SITU MONITORING OF FABRICATION OF INTEGRATED COMPUTATIONAL ELEMENTS

CLAIM OF PRIORITY

This application is a U.S. National Stage of International Application No. PCT/US2013/077690, filed Dec. 24, 2013.

BACKGROUND

The subject matter of this disclosure is generally related to fabrication of an integrated computational element (ICE) used in optical analysis tools for analyzing a substance of interest, for example, crude petroleum, gas, water, or other wellbore fluids. For instance, the disclosed ICE fabrication uses a combination of measurement techniques for in-situ monitoring of the ICE fabrication.

Information about a substance can be derived through the interaction of light with that substance. The interaction changes characteristics of the light, for instance the frequency (and corresponding wavelength), intensity, polarization, and/or direction (e.g., through scattering, absorption, reflection or refraction). Chemical, thermal, physical, mechanical, optical or various other characteristics of the substance can be determined based on the changes in the characteristics of the light interacting with the substance. As such, in certain applications, one or more characteristics of crude petroleum, gas, water, or other wellbore fluids can be derived in-situ, e.g., downhole at well sites, as a result of the interaction between these substances and light.

Integrated computational elements (ICEs) enable the measurement of various chemical or physical characteristics through the use of regression techniques. An ICE selectively weights, when operated as part of optical analysis tools, light modified by a sample in at least a portion of a wavelength range such that the weightings are related to one or more characteristics of the sample. An ICE can be an optical substrate with multiple stacked dielectric layers (e.g., from about 2 to about 50 layers), each having a different complex refractive index from its adjacent layers. The specific number of layers, N, the optical properties (e.g. real and imaginary components of complex indices of refraction) of the layers, the optical properties of the substrate, and the physical thickness of each of the layers that compose the ICE are selected so that the light processed by the ICE is related to one or more characteristics of the sample. Because ICEs extract information from the light modified by a sample passively, they can be incorporated in low cost and rugged optical analysis tools. Hence, ICE-based downhole optical analysis tools can provide a relatively low cost, rugged and accurate system for monitoring quality of wellbore fluids, for instance.

Errors in fabrication of some constituent layers of an ICE design can degrade the ICE's target performance. In most cases, deviations of <0.1%, and even 0.01% or 0.0001%, from point by point design values of the optical characteristics (e.g., complex refractive indices), and/or physical characteristics (e.g., thicknesses) of the formed layers of the ICE can reduce the ICE's performance, in some cases to such an extent, that the ICE becomes operationally useless. Those familiar or currently practicing in the art will readily appreciate that the ultra-high accuracies required by ICE designs challenge the state of the art in thin film measurement techniques.

DESCRIPTION OF DRAWINGS

FIGS. 1A-1C show multiple configurations of an example of a system for analyzing wellbore fluids that uses a well logging tool including an ICE.

Like reference symbols in the various drawings indicate like elements.

DETAILED DESCRIPTION

Technologies are described for in-situ adjusting ICE fabrication based on values of optical characteristics (e.g., complex refractive indices) and physical characteristics (e.g., thicknesses) of formed layers of an ICE that are determined from results of at least two different measurement techniques performed during the ICE fabrication.

The disclosed technologies can be used to implement ICE fabrication that can be more accurate than conventional ICE fabrication. For instance, a potential advantage of the disclosed technologies is that by performing multiple in-situ measurements, complex refractive indices and thicknesses of the formed layers are determined in real-time or near real-time, which in turn are used to adjust forming of layers of the ICE remaining to be formed. Moreover, the complex refractive indices and thicknesses of the formed layers determined from results of the multiple in-situ measurements are more accurate than if they were conventionally determined from results of a single in-situ measurement, as described in detail in Section (3). More accurate in-situ monitoring of ICE fabrication translates into improved batch yield and yield consistency batch-to-batch relative to conventional ICE fabrication.

Prior to describing example implementations of the disclosed technologies for ICE fabrication, the following technologies are described below: in Section (1)—optical analysis tools based on ICE along with examples of their use in oil/gas exploration, and in Section (2)—techniques for designing an ICE.

(1) ICE-Based Analysis of Wellbore Fluids

Figure 1A:
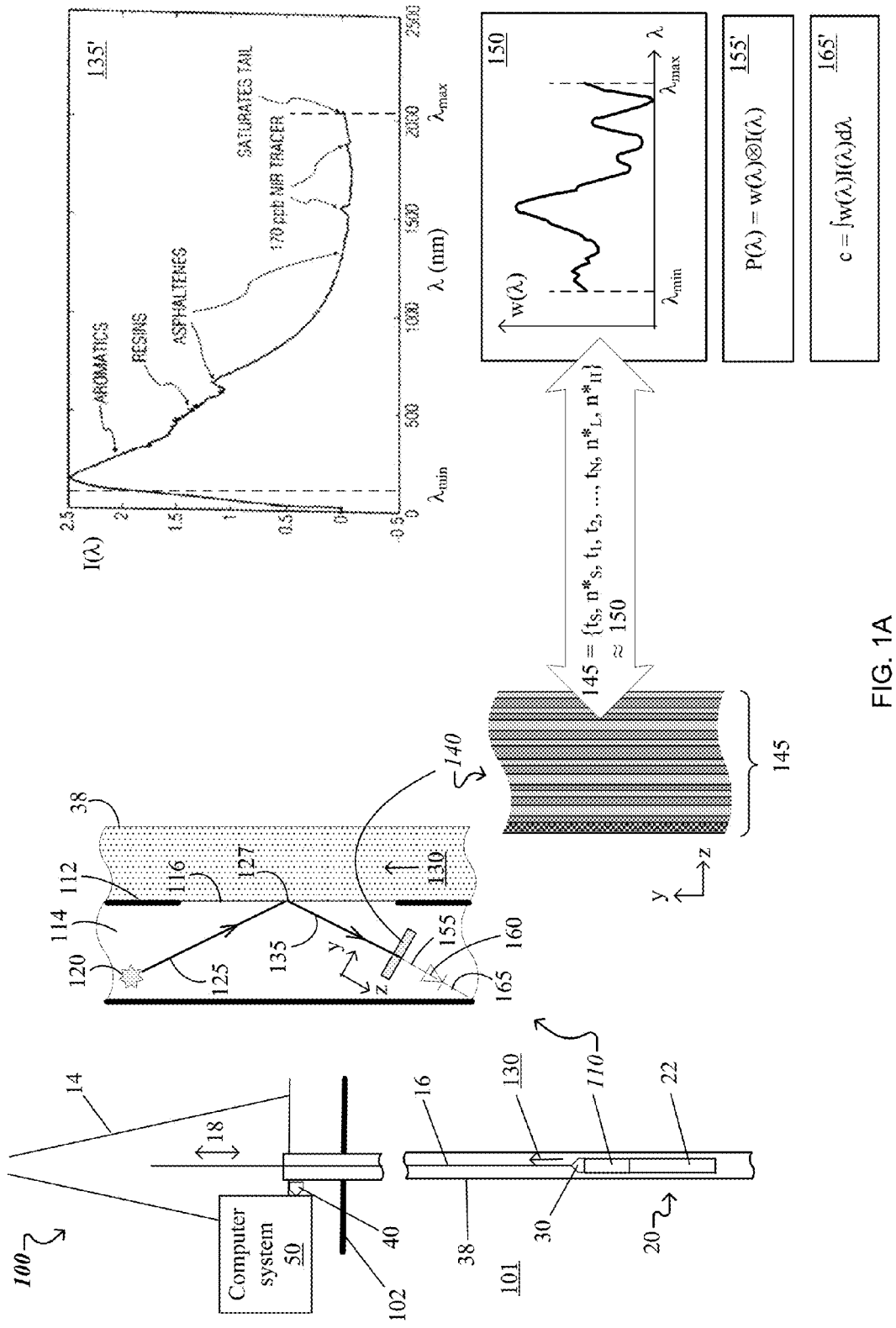

FIGS. 1A-1C show multiple configurations 100, 100', 100" of an example of a system for analyzing wellbore fluids 130, such that analyses are generated from measurements taken with a well logging tool 110 configured as an ICE-based optical analysis tool. The disclosed system also is referred to as a well logging system.

Each of the configurations 100, 100', 100" of the well logging system illustrated in FIGS. 1A-1C includes a rig 14 above the ground surface 102 and a wellbore 38 below the ground surface. The wellbore 38 extends from the ground surface into the earth 101 and generally passes through multiple geologic formations. In general, the wellbore 38 can contain wellbore fluids 130. The wellbore fluids 130 can be crude petroleum, mud, water or other substances and combinations thereof. Moreover, the wellbore fluids 130 may be at rest, or may flow toward the ground surface 102, for instance. Additionally, surface applications of the well logging tool 110 may include water monitoring and gas and crude transportation and processing.

FIG. 1A shows a configuration 100 of the well logging system which includes a tool string 20 attached to a cable 16 that can be lowered or raised in the wellbore 38 by draw works 18. The tool string 20 includes measurement and/or logging tools to generate and log information about the wellbore fluids 130 in the wellbore 38. In the configuration 100 of the well logging system, this information can be generated as a function of a distance (e.g., a depth) with respect to the ground surface 102. In the example illustrated in FIG. 1A, the tool string 20 includes the well logging tool 110, one or more additional well logging tool(s) 22, and a telemetry transmitter 30. Each of the well logging tools 110 and 22 measures one or more characteristics of the wellbore fluids 130. In some implementations, the well logging tool 110 determines values of the one or more characteristics in real time and reports those values instantaneously as they occur in the flowing stream of wellbore fluids 130, sequentially to or simultaneously with other measurement/logging tools 22 of the tool string 20.

FIG. 1B shows another configuration 100' of the well logging system which includes a drilling tool 24 attached to a drill string 16'. The drilling tool 24 includes a drill bit 26, the ICE-based well logging tool 110 configured as a measurement while drilling (MWD) and/or logging while drilling (LWD) tool, and the telemetry transmitter 30. Drilling mud is provided through the drill string 16' to be injected into the borehole 38 through ports of the drill bit 26. The injected drilling mud flows up the borehole 38 to be returned above the ground level 102, where the returned drilling mud can be resupplied to the drill string 16' (not shown in FIG. 1B). In this case, the MWD/LWD-configured well logging tool 110 generates and logs information about the wellbore fluids 130 (e.g., drilling mud in this case) adjacent the working drill bit 26.

FIG. 1C shows yet another configuration 100" of the well logging system which includes a permanent installation adjacent to the borehole 38. In some implementations, the permanent installation is a set of casing collars that reinforce the borehole 38. In this case, a casing collar 28 from among the set of casing collars supports the well logging tool 110 and the telemetry transmitter 30. In this manner, the well logging tool 110 determines and logs characteristics of the wellbore fluids 130 adjacent the underground location of the casing collar 28.

In each of the above configurations 100, 100' and 100" of the well logging system, the values of the one or more characteristics measured by the well logging tool 110 are provided (e.g., as a detector signal 165) to the telemetry transmitter 30. The latter communicates the measured values to a telemetry receiver 40 located above the ground surface 102. The telemetry transmitter 30 and the telemetry receiver 40 can communicate through a wired or wireless telemetry channel. In some implementations of the system configurations 100, 100' illustrated in FIGS. 1A and 1B, e.g., in slickline or coiled tubing applications, measurement data generated by the well logging tool 110 can be written locally to memory of the well logging tool 110.

The measured values of the one or more characteristics of the wellbore fluids 130 received by the telemetry receiver 40 can be logged and analyzed by a computer system 50 associated with the rig 14. In this manner, the measurement values provided by the well logging tool 110 can be used to generate physical and chemical information about the wellbore fluids 130 in the wellbore 38.

Referring again to FIG. 1A, the well logging tool 110 includes a light source 120, an ICE 140 and an optical transducer 160. The well logging tool 110 has a frame 112 such that these components are arranged in an enclosure 114 thereof. A cross-section of the well logging tool 110 in a plane perpendicular to the page can vary, depending on the space available. For example, the well logging tool's cross-section can be circular or rectangular, for instance. The well logging tool 110 directs light to the sample 130 through an optical interface 116, e.g., a window in the frame 112. The well logging tool 110 is configured to probe the sample 130 (e.g., the wellbore fluids stationary or flowing) in the wellbore 38 through the optical interface 116 and to determine an amount (e.g., a value) of a given characteristic (also referred to as a characteristic to be measured) of the probed sample 130. The characteristic to be measured can be any one of multiple characteristics of the sample 130 including concentration of a given substance in the sample, a gas-oil-ratio (GOR), pH value, density, viscosity, etc.

The light source 120 outputs light with a source spectrum over a particular wavelength range, from a minimum wavelength $\lambda_{min}$ to a maximum wavelength $\lambda_{max}$. In some implementations, the source spectrum can have non-zero intensity over the entire or most of the wavelength range $\lambda_{max}$-$\lambda_{min}$. In some implementations, the source spectrum extends through UV-vis (0.2-0.8 µm) and near-IR (0.8-2.5 µm) spectral ranges. Alternatively, or additionally, the source spectrum extends through near-IR and mid-IR (2.5-25 µm) spectral ranges. In some implementations, the source spectrum extends through near-IR, mid-IR and far-IR (25-100 µm) spectral ranges. In some implementations, the light source 120 is tunable and is configured in combination with time resolved signal detection and processing.

The light source 120 is arranged to direct a probe beam 125 of the source light towards the optical interface 116 where it illuminates the sample 130 at a location 127. The source light in the probe beam 125 interacts with the sample 130 and reflects off it as light modified by the sample 130. The light modified by the sample has a modified spectrum $I(\lambda)$ 135' over the particular wavelength range. In the reflective configuration of the well logging tool 110 illustrated in FIG. 1A (i.e., where the light to be analyzed reflects at the sample/window interface), the modified spectrum $I(\lambda)$ 135' is a reflection spectrum associated with the sample 130. In a transmission configuration of the well logging tool 110 (not shown in FIG. 1A), the probe beam is transmitted through the sample as modified light, such that the modified spectrum $I(\lambda)$ 135' is a transmission spectrum associated with the sample.

In general, the modified spectrum $I(\lambda)$ 135' encodes information about multiple characteristics associated with the sample 130, and more specifically the encoded information relates to current values of the multiple characteristics. In the example illustrated in FIG. 1A, the modified spectrum 135' contains information about one or more characteristics of the wellbore fluids 130.

With continued reference to FIG. 1A, and the Cartesian coordinate system provided therein for reference, the ICE 140 is arranged to receive a beam 135 of the sample modified light, and is configured to process it and to output a beam 155 of processed light. The beam 135 of sample modified light is incident on a first surface of the ICE 140 along the z-axis, and the beam 155 of processed light is output along the z-axis after transmission through the ICE 140. Alternatively or additionally, the beam 155 (or an additional reflected beam) of processed light can be output after reflection off the first surface of the ICE 140. The ICE 140 is configured to process the sample modified light by weighting it in accordance with an optical spectrum $w(\lambda)$ 150 associated with a characteristic to be measured.

The optical spectrum $w(\lambda)$ 150 is determined offline by applying conventional processes to a set of calibration spectra $I(\lambda)$ of the sample which correspond to respective known values of the characteristic to be measured. As illustrated by optical spectrum w(λ) 150, optical spectrums generally may include multiple local maxima (peaks) and minima (valleys) between $\lambda_{min}$ and $\lambda_{max}$. The peaks and valleys may have the same or different amplitudes. For instance, an optical spectrum w(λ) can be determined through regression analysis of $N_c$ calibration spectra $I_j(\lambda)$ of a sample, where j=1, . . . , $N_c$, such that each of the calibration spectra $I_j(\lambda)$ corresponds to an associated known value of a given characteristic for the sample. A typical number $N_c$ of calibration spectra $I_j(\lambda)$ used to determine the optical spectrum w(λ) 150 through such regression analysis can be $N_c$=10, 40 or 100, for instance. The regression analysis outputs, within the $N_c$ calibration spectra $I_j(\lambda)$, a spectral pattern that is unique to the given characteristic. The spectral pattern output by the regression analysis corresponds to the optical spectrum w(λ) 150. In this manner, when a value of the given characteristic for the sample is unknown, a modified spectrum $I_u(\lambda)$ of the sample is acquired by interacting the probe beam 125 with the sample 130, then the modified spectrum $I_u(L)$ is weighted with the ICE 140 to determine a magnitude of the spectral pattern corresponding to the optical spectrum w(λ) 150 within the modified spectrum $I_u(\lambda)$. The determined magnitude is proportional to the unknown value of the given characteristic for the sample.

For example, the sample can be a mixture (e.g., the wellbore fluid 130) containing substances X, Y and Z, and the characteristic to be measured for the mixture is concentration $c_X$ of substance X in the mixture. In this case, calibration spectra $I_j(\lambda)$ were acquired for $N_c$ samples of the mixture having respectively known concentration values for each of the substances contained in the $N_c$ samples. By applying regression analysis to the $N_c$ calibration spectra $I_j(\lambda)$, a first spectral pattern that is unique to the concentration $c_X$ of the X substance can be detected (recognized), such that the first spectral pattern corresponds to a first optical spectrum $w_{cX}(\lambda)$ associated with a first ICE, for example. Similarly, second and third spectral patterns that are respectively unique to concentrations $c_Y$ and $c_Z$ of the Y and Z substances can also be detected, such that the second and third spectral patterns respectively correspond to second and third optical spectra $w_{cY}(\lambda)$ and $w_{cZ}(\lambda)$ respectively associated with second and third ICEs. In this manner, when a new sample of the mixture (e.g., the wellbore fluid 130) has an unknown concentration $c_X$ of the X substance, for instance, a modified spectrum $I_u(\lambda)$ of the new sample can be acquired by interacting the probe beam with the mixture, then the modified spectrum Iu(λ) is weighted with the first ICE to determine a magnitude of the first spectral pattern within the modified spectrum $I_u(\lambda)$. The determined magnitude is proportional to the unknown value of the concentration $c_X$ of the X substance for the new sample.

Referring again to FIG. 1A, the ICE 140 includes N layers of materials stacked on a substrate, such that complex refractive indices of adjacent layers are different from each other. The total number of stacked layers can be between 6 and 50, for instance. The substrate material can be BK7, diamond, Ge, ZnSe (or other transparent dielectric material), and can have a thickness in the range of 0.02-2 mm, for instance, to insure structural integrity of the ICE 140.

Throughout this specification, a complex index of refraction (or complex refractive index) n* of a material has a complex value, Re(n*)+iIm(n*). Re(n*) represents a real component of the complex index of refraction responsible for refractive properties of the material, and Im(n*) represents an imaginary component of the complex index of refraction (also known as extinction coefficient κ) responsible for absorptive properties of the material. In this specification, when it is said that a material has a high complex index of refraction $n^*_H$ and another material has a low complex index of refraction $n^*_L$, the real component $Re(n^*_H)$ of the high complex index of refraction $n^*_H$ is larger than the real component $Re(n^*_L)$ of the low complex index of refraction $n^*_L$, $Re(n^*_H) > Re(n^*_L)$. Materials of adjacent layers of the ICE are selected to have a high complex index of refraction $n^*_H$ (e.g., Si), and a low complex index of refraction $n^*_L$ (e.g., $SiO_2$). Here, $Re(n^*_{Si}) \approx 2.4 > Re(n^*_{SiO2}) \approx 1.5$. For other material pairings, however, the difference between the high complex refractive index $n^*_H$ and low complex refractive index $n^*_L$ may be much smaller, e.g., $Re(n^*_H) \approx 1.6 > Re(n^*_L) \approx 1.5$. The use of two materials for fabricating the N layers is chosen for illustrative purposes only. For example, a plurality of materials having different complex indices of refraction, respectively, can be used. Here, the materials used to construct the ICE are chosen to achieve a desired optical spectrum w(λ) 150.

A set of design parameters 145—which includes the total number of stacked layers N, the complex refractive indices $n^*_H, n^*_L$ of adjacent stacked layers, and the thicknesses of the N stacked layers t(1), t(2), t(N−1), t(N)—of the ICE 140 can be chosen (as described below in connection with FIG. 2) to be spectrally equivalent to the optical spectrum w(λ) 150 associated with the characteristic to be measured. As such, an ICE design includes a set 145 of thicknesses {t(i), i=1, . . . , N} of the N layers stacked on the substrate that correspond to the optical spectrum w(λ) 150.

In view of the above, the beam 155 of processed light output by the ICE 140 has a processed spectrum P(λ)= w(λ)⊗(λ) 155' over the wavelength range $\lambda_{max}$-$\lambda_{min}$, such that the processed spectrum 155' represents the modified spectrum I(λ) 135' weighted by the optical spectrum w(λ) 150 associated with the characteristic to be measured.

The beam 155 of processed light is directed from the ICE 140 to the optical transducer 160, which detects the processed light and outputs an optical transducer signal 165. A value (e.g., a voltage) of the optical transducer signal 165 is a result of an integration of the processed spectrum 155' over the particular wavelength range and is proportional to the unknown value "c" 165' of the characteristic to be measured for the sample 130.

In some implementations, the well logging tool 110 can include a second ICE (not shown in FIG. 1A) associated with a second ICE design that includes a second set of thicknesses {t'(i), i=1, . . . , N'} of a second total number N' of layers, each having a different complex refractive index from its adjacent layers, the complex refractive indices and the thicknesses of the N' layers corresponding to a second optical spectrum w'(λ). Here, the second optical spectrum w'(λ) is associated with a second characteristic of the sample 130, and a second processed spectrum represents the modified spectrum I(λ) 135' weighted by the second optical spectrum w'(λ), such that a second value of a second detector signal is proportional to a value of the second characteristic for the sample 130.

In some implementations, the determined value 165' of the characteristic to be measured can be logged along with a measurement time, geo-location, and other metadata, for instance. In some implementations, the detector signal 165, which is proportional to a characteristic to be measured by the well logging tool 110, can be used as a feedback signal to adjust the characteristic of the sample, to modify the sample or environmental conditions associated with the sample, as desired.

Characteristics of the wellbore fluids 130 that can be related to the modified spectrum 135' through the optical spectra associated with the ICE 140 and other ICEs (not shown in FIG. 1A) are concentrations of one of asphaltene, saturates, resins, aromatics; solid particulate content; hydrocarbon composition and content; gas composition C1-C6 and content: $CO_2$, $H_2S$ and correlated PVT properties including GOR, bubble point, density; a petroleum formation factor; viscosity; a gas component of a gas phase of the petroleum; total stream percentage of water, gas, oil, solid articles, solid types; oil finger printing; reservoir continuity; oil type; and water elements including ion composition and content, anions, cations, salinity, organics, pH, mixing ratios, tracer components, contamination, or other hydrocarbon, gas, solids or water property.

(2) Aspects of ICE Design

Aspects of a process for designing an ICE associated with a characteristic to be measured (e.g., one of the characteristics enumerated above) are described below. Here, an input of the ICE design process is a theoretical optical spectrum $w_{th}(\lambda)$ associated with the characteristic. An output of the ICE design process is an ICE design that includes specification of (1) a substrate and a number N of layers to be formed on the substrate, each layer having a different complex refractive index from its adjacent layers; and (2) complex refractive indices and thicknesses of the substrate and layers that correspond to a target optical spectrum $w_t(\lambda)$. The target optical spectrum $w_t(\lambda)$ is different from the theoretical optical spectrum $w_{th}(\lambda)$ associated with the characteristic, such that the difference between the target and theoretical optical spectra cause degradation of a target performance relative to a theoretical performance of the ICE within a target error tolerance. The target performance represents a finite accuracy with which an ICE having the target optical spectrum $w_t(\lambda)$ is expected to predict known values of the characteristic corresponding to a set of validation spectra of a sample with a finite (non-zero) error. Here, the predicted values of the characteristic are obtained through integration of the validation spectra of the sample respectively weighted by the ICE with the target optical spectrum $w_t(\lambda)$. The theoretical performance represents the maximum accuracy with which the ICE—if it had the theoretical optical spectrum $w_{th}(\lambda)$—would predict the known values of the characteristic corresponding to the set of validation spectra of the sample. Here, the theoretically predicted values of the characteristic would be obtained through integration of the validation spectra of the sample respectively weighted by the ICE, should the ICE have the theoretical optical spectrum $w_{th}(\lambda)$.

Figure 2:
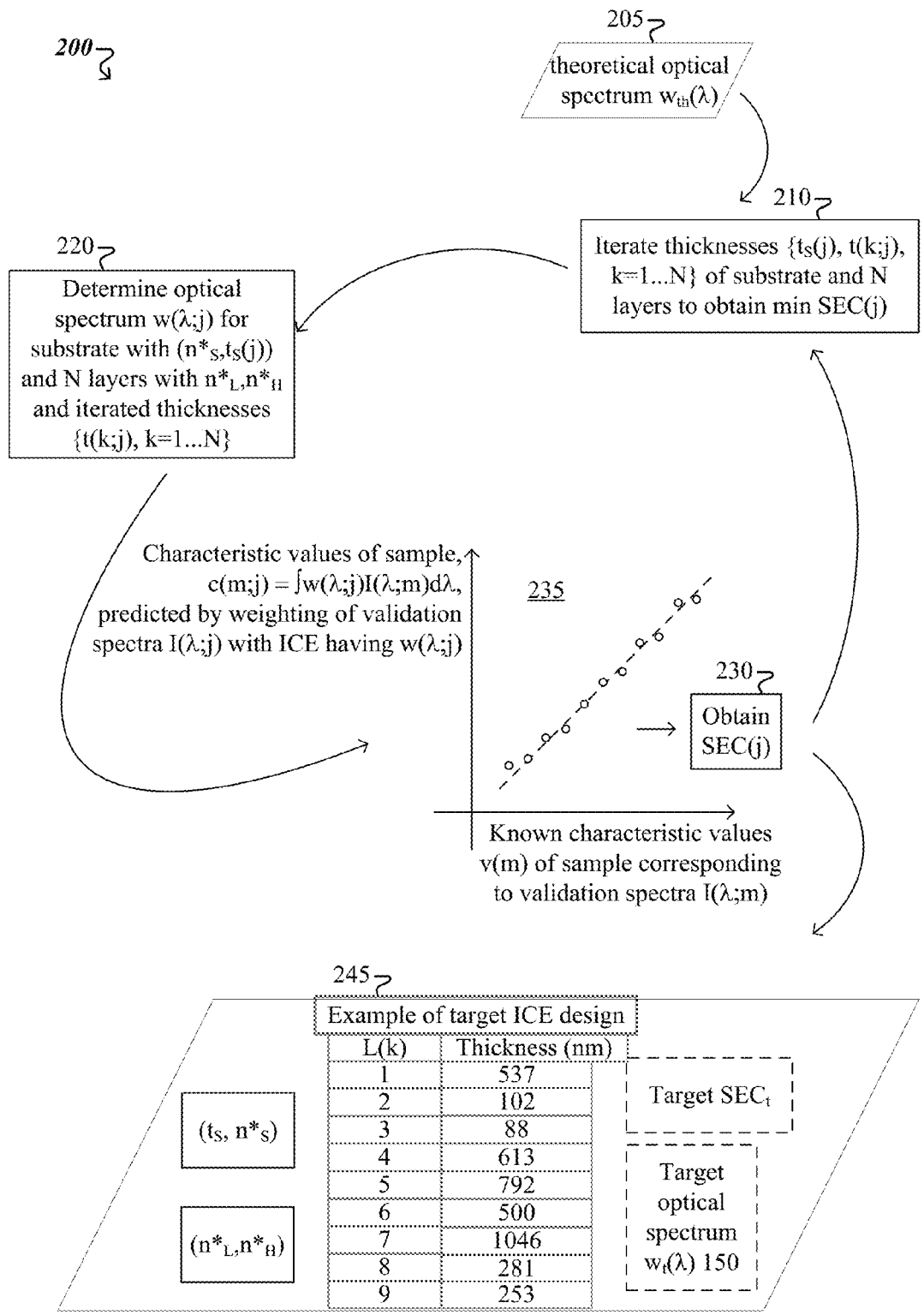
FIG. 2 is a flowchart showing an example of a process for designing an ICE.

FIG. 2 is a flow chart of an example of a process 200 for generating an ICE design. One of the inputs to the process 200 is a theoretical optical spectrum $w_{th}(\lambda)$ 205. For instance, to design an ICE for measuring concentration of a substance X in a mixture, a theoretical optical spectrum $w_{th}(\lambda)$, associated with the concentration of the substance X in the mixture, is accessed, e.g., in a data repository. As described above in this specification, the accessed theoretical optical spectrum $w_t(\lambda)$ corresponds to a spectral pattern detected offline, using a number $N_c$ of calibration spectra of the mixture, each of the $N_c$ calibration spectra corresponding to a known concentration of the substance X in the mixture. An additional input to the process 200 is a specification of materials for a substrate and ICE layers. Materials having different complex refractive indices, respectively, are specified such that adjacent ICE layers are formed from materials with different complex refractive indices. For example, a first material (e.g., Si) having a high complex refractive index $n^*_H$ and a second material (e.g., $SiO_x$) having a low complex refractive index $n^*_L$ are specified to alternately form the ICE layers. As another example, a layer can be made from high index material (e.g., Si), followed by a layer made from low index material (e.g., $SiO_x$), followed by a layer made from a different high index material (e.g., Ge), followed by a layer made from a different low index material ($MgF_2$), etc. The iterative design process 200 is performed in the following manner.

At 210 during the $j^{th}$ iteration of the design process 200, thicknesses $\{t_S(j), t(1;j), t(2;j), \ldots, t(N-1;j), t(N;j)\}$ of the substrate and a number N of layers of the ICE are iterated.

At 220, a $j^{th}$ optical spectrum $w(\lambda;j)$ of the ICE is determined corresponding to complex refractive indices and previously iterated thicknesses $\{t_S(j), t(1;j), t(2;j), \ldots, t(N-1;j), t(N;j)\}$ of the substrate and the N layers, each having a different complex refractive index from its adjacent layers. The iterated thicknesses of the substrate and the N layers are used to determine the corresponding $j^{th}$ optical spectrum $w(\lambda;j)$ of the ICE in accordance with conventional techniques for determining spectra of thin film interference filters.

At 230, performance of the ICE, which has the $j^{th}$ optical spectrum $w(\lambda;j)$ determined at 220, is obtained. To do so, a set of validation spectra of a sample is accessed, e.g., in a data repository. Respective values of a characteristic of the sample are known for the validation spectra. For instance, each of $N_v$ validation spectra $I(\lambda;m)$ corresponds to a value $v(m)$ of the characteristic of the sample, where $m=1, \ldots, N_v$. In the example illustrated in FIG. 2, $N_v=11$ validation spectra, respectively corresponding to 11 known values of the characteristic to be measured for the sample, are being used.

Graph 235 shows (in open circles) values $c(m;j)$ of the characteristic of the sample predicted by integration of the validation spectra $I(\lambda;m)$ weighted with the ICE, which has the $j^{th}$ optical spectrum $w(\lambda;j)$, plotted against the known values $v(m)$ of the characteristic of the sample corresponding to the validation spectra $I(\lambda;m)$. The predicted values $c(m;1)$ of the characteristic are found by substituting, in formula 165' of FIG. 1A, (1) the spectrum $I(\lambda)$ 135' of sample modified light with the respective validation spectra $I(\lambda;m)$ and (2) the target spectrum $w_t(\lambda)$ 150 with the $j^{th}$ optical spectrum $w(\lambda;j)$. In this example, performance of the ICE, which has the $j^{th}$ optical spectrum $w(\lambda;j)$, is quantified in terms of a weighted measure of distances from each of the open circles in graph 235 to the dashed-line bisector between the x and y axes. This weighted measure is referred to as the standard calibration error (SEC) of the ICE. For instance, an ICE having the theoretical spectrum $w_{th}(\lambda)$ has a theoretical $SEC_{th}$ that represents a lower bound for the SEC(j) of the ICE having the $j^{th}$ spectrum $w(\lambda;j)$ determined at 220 during the $j^{th}$ iteration of the design process 200: $SEC(j) > SEC_{th}$.

In this specification, the SEC is chosen as a metric for evaluating ICE performance for the sake of simplicity. Note that there are other figures of merit that may be used to evaluate performance of ICE, as is known in the art. For example, sensitivity—which is defined as the slope of characteristic change as a function of signal strength—can also be used to evaluate ICE performance. As another example, standard error of prediction (SEP)—which is defined in a similar manner to the SEC except it uses a different set of validation spectra—can be used to evaluate ICE performance. Any of the figure(s) of merit known in the art is/are evaluated in the same general way by comparing theoretical performance with that actually achieved. Which figure(s) of merit or combinations are used to evaluate ICE performance is determined by the specific ICE design.

The iterative design process 200 continues by iterating, at 210, the thicknesses of the substrate and the N layers. The iterating is performed such that a $(j+1)^{th}$ optical spectrum $w(\lambda;j+1)$—determined at 220 from the newly iterated thicknesses—causes, at 230, improvement in performance of the ICE, to obtain $SEC(j+1) < SEC(j)$. In some implementations, the iterative design process 200 is stopped when the ICE's performance reaches a local maximum, or equivalently, the SEC of the ICE reaches a local minimum. For example, the iterative process 200 can be stopped at the $(j+1)^{th}$ iteration when the current SEC(j+1) is larger than the last SEC(j), SEC(j+1)>SEC(j). In some implementations, the iterative design process 200 is stopped when, for a given number of iterations, the ICE's performance exceeds a specified threshold performance for a given number of iterations. For example, the iterative design process 200 can be stopped at the $j^{th}$ iteration when three consecutive SEC values decrease monotonously and are less than a specified threshold value: $SEC_0 > SEC(j-2) > SEC(j-1) > SEC(j)$.

In either of these cases, an output of the iterative process 200 represents a target ICE design 245 to be used for fabricating an ICE 140, like the one described in FIG. 1A, for instance. The ICE design 245 includes specification of (1) a substrate and N layers, each having a different complex refractive index from its adjacent layers, and (2) complex refractive indices $n^*_S$, $n^*_H$, $n^*_L$ and thicknesses $\{t_S(j), t(1;j), t(2;j), t(N-1;j), t(N;j)\}$ of the substrate and N layers corresponding to the $j^{th}$ iteration of the process 200. Additional components of the ICE design are the optical spectrum $w(\lambda;j)$ and the SEC(j)—both determined during the $j^{th}$ iteration based on the thicknesses $\{t_S(j), t(1;j), t(2;j), t(N-1;j), t(N;j)\}$. As the ICE design 245 is used as input for fabrication processes described herein, the iteration index j—at which the iterative process 200 terminates—is dropped from the notations used for the components of the ICE design.

In this manner, the thicknesses of the substrate and the N layers associated with the ICE design 245 are denoted $\{t_S, t(1), t(2), t(N-1), t(N)\}$ and are referred to as the target thicknesses. The optical spectrum associated with the ICE design 245 and corresponding to the target thicknesses is referred to as the target optical spectrum $w_t(\lambda)$ 150. The SEC associated with the ICE design 245—obtained in accordance with the target optical spectrum $w_t(\lambda)$ 150 corresponding to the target thicknesses—is referred to as the target $SEC_t$. In the example illustrated in FIG. 2, the ICE design 245 has a total of N=9 alternating Si and $SiO_2$ layers, with complex refractive indices $n_{Si}$, $n_{SiO2}$, respectively. The layers' thicknesses (in nm) are shown in the table. An ICE fabricated based on the example of ICE design 245 illustrated in FIG. 2 is used to predict value(s) of concentration of substance X in wellbore fluids 130.

(3) Technologies for Adjusting Fabrication of ICE

As described above in connection with FIG. 2, an ICE design specifies a number of material layers), each having a different complex refractive index from its adjacent layers. An ICE fabricated in accordance with the ICE design has (i) a target optical spectrum $w_t(\lambda)$ and (ii) a target performance $SEC_t$, both of which correspond to the complex refractive indices and target thicknesses of a substrate and a total number of layers specified by the ICE design. Performance of the ICE fabricated in accordance with the ICE design can be very sensitive to actual values of the complex refractive indices and thicknesses obtained during deposition. For a wide variety of reasons, the actual values of the complex refractive indices of materials to be deposited and/or the rate(s) of the deposition may drift within a fabrication batch or batch-to-batch, or may be affected indirectly by errors caused by measurement systems used to control the foregoing fabrication parameters. For example, materials used for deposition (Si, $SiO_2$) may be differently contaminated, or react differently due to different chamber conditions (e.g., pressure or temperature). For some layers of the ICE design 245, a small error, e.g., 0.1% or 0.001%, in the thickness of a deposited layer can result in a reduction in the performance of an ICE associated with the ICE design 245 below an acceptable threshold. Effects of fabrication errors on the performance of fabricated ICEs are minimized by monitoring the ICE fabrication.

Historically, the complex refractive indices and thicknesses of layers of a fabricated ICE are determined by using a suite of measurement techniques such as, e.g., ellipsometry, spectroscopy, optical microscopy and scanning electronic microscopy and the like, that are performed ex-situ. Results of such ex-situ measurements are combined to determine the complex refractive indices and thicknesses of the fabricated ICEs' layers. In this manner, adjustments can be made to ICE fabrication of subsequent batches based on comparisons between determined values of the complex refractive indices and thicknesses of the fabricated ICEs' layers and their respective target values. Ex-situ monitoring techniques of ICE fabrication have many advantages. In general, the ex-situ measurements can be performed over time and on highly accurate instruments. An ex-situ measurement, for example, of physical or optical characteristics of a fabricated ICE's layers may take many days to perform. Ex-situ instruments are also generally used in a known and clean environment, such as a laboratory environment, which enables measurements to be made generally free of degrading interferences (e.g. background interferent blackbody radiation or vibrations that degrade delicate optical instruments). Finally, there are few constraints on the size of the ex-situ instrumentation used so that large but precise instruments can be employed to attain the stringent and demanding accuracies required for viable ICE fabrication. It is because of the ultra-high precision required by ICE designs that ex-situ measurements have been historically used to fabricate ICE. The primary disadvantage of ex-situ measurements is the fabrication process may change over time creating the need to predict current ICE layer optical and physical characteristics based on historical ex-situ measurements and trends. This can often result in poor ICE fabrication yields and multiple attempts to create a single ICE design, especially for ICE designs whose performance is particularly sensitive to changes in the optical and/or physical characteristics of the constituent layers. In the latter case, relatively small errors in the ex-situ measurement predictions can often prevent the fabrication of viable ICE designs as the run to run changes are larger than the ICE design tolerances.

In-situ measurements offer the potential to improve ICE fabrication yields by measuring the ICE layer optical and/or physical properties during the present run instead of the previous run(s). Instruments used to perform in-situ measurements include physical thickness monitors (e.g. vibrating crystal monitors), single and multiple wavelength optical monitors, in-situ spectrometers, in-situ ellipsometers, and in-situ compositional monitors (e.g. residual gas monitors). There are potential issues with in-situ measurements particularly as they relate to ICE fabrication and the ultra-high accuracies required for viable ICE designs. In general, the vacuum deposition environment in which ICEs are fabricated creates many and substantial barriers to ultra-high precision measurements.

For example, the large path lengths—on the order of a meter or more between deposition sources and ICE substrates required for uniform deposition of the ICE layers—restrict the amount of light which can be successfully transmitted and collected by all the in-situ optically based instruments such as single and multiple wavelength optical monitors, spectrometers, and ellipsometers. Here, collected light intensities can easily be one or two orders of magnitude lower than their ex-situ counterparts, thus substantially impacting the signal-to-noise (S/N) ratios and accuracies of the optical measurements. In addition, the high vibration environment associated with vacuum deposition systems in which ICEs are fabricated causes the optical beams to vibrate across or be misaligned with the optical detectors of the instruments further degrading their S/N ratios and measurement accuracies. The vibrations associated with the vacuum deposition systems also affect the position and tooling factors employed degrading the accuracy further. Thermal sources of the high temperature deposition environments in which ICEs are fabricated generate blackbody radiation generally in the visible, near-infrared (IR), and IR regions of the electromagnetic spectrum where many ICEs are designed to operate in. This blackbody radiation interferes with the optical beam associated with the optically based instruments (single and multiple wavelength optical monitors, spectrometers and ellipsometers) and degrades their accuracy further. In situ crystal monitors, such as vibrating crystal monitors, accumulate mass from the thin film deposition process which degrades their calibration and results in inaccurate readings. Additionally, the physical constraints of vacuum deposition systems in which ICEs are fabricated, including the requirement that the instrumentation itself not be coated with the thin films, further restricts the in-situ instrumentation that can be employed and its accuracy.

It can be appreciated by those familiar with the art that the ultrahigh (typically <<0.1%) accuracies required by most ICE designs can only be achieved by ex-situ instrumentation. For these reasons primarily relating to the ultra-high precision required for viable ICE creation, ICE has historically been made primarily using ex-situ instrumentation. In fact, efforts to employ any one of the foregoing in-situ measurement techniques (e.g. physical thickness monitoring or in-situ spectroscopy) have been historically unsuccessful in increasing the ICE fabrication yields to any significant extent. Typical physical or optical characteristics accuracies obtained with these in-situ instruments was generally substantially above the <<0.1% or 0.001% required for most ICE designs of interest.

The accuracy limitations associated with in-situ monitoring of ICE fabrication can be overcome, in accordance with technologies disclosed herein, by employing at least two and most preferably three of the foregoing in-situ measurement techniques. While it is counter intuitive that one can take two or more relatively inaccurate measurements to yield a precise determination, this discovery has been successfully used on multiple occasions to substantially increase ICE fabrication yields. For instance, it has been determined that ellipsometry is very useful in monitoring complex refractive indices and thicknesses of ICE stacks have one or two layers, but becomes insensitive and inaccurate for monitoring ICE stacks with more layers. Spectroscopy, on the other hand, is relatively insensitive for monitoring ICE stacks with one or two layers, but more accurate and appropriate for monitoring ICE stacks with a larger number of layers. Further, optical monitoring is generally inaccurate for monitoring ICE stacks that are optically "thin", either because their physical thickness is much less than quarter wave, because they include mostly transparent films. Furthermore, physical thickness monitors (such as, e.g., vibrating crystals) are generally less accurate for monitoring ICE stack that include thicker layers.

In accordance with the disclosed technologies, information from measurements of two or more of the foregoing types can be combined to generate accurate in-situ monitoring of the ICE layers by appropriately weighting results obtained from respective measurements of different types that were performed at the same point(s) of the ICE fabrication process, in some implementations. For example, each of ellipsometry, optical monitoring and spectroscopy can be performed in-situ upon depositing a small, an intermediate and a large number of layers of the ICE. Here, results of the ellipsometry measurements are weighted the heaviest when the three in-situ measurements are performed upon depositing the small number of layers; results of the optical monitoring are weighted the heaviest when the three in-situ measurements are performed upon depositing the intermediate number of layers; and results of the spectroscopy are weighted the heaviest when the three in-situ measurements are performed upon depositing the large number of layers. In other implementations, only most accurate one(s) of the measurements of the foregoing types are performed at multiple points of the ICE fabrication process. For example, only ellipsometry is performed upon depositing the small number of layers; only optical monitoring is performed upon depositing the intermediate number of layers; and only spectroscopy is performed upon depositing the large number of layers. Many other combinations of measurements of two or more types are described in detail below.

In this manner, accuracy of the complex refractive indices and thicknesses of the formed layers determined by combining results from at least two in-situ measurement techniques is improved relative to the accuracy obtained by performing a single in-situ measurement of any one of the types described above. Throughout this specification, determining a complex refractive index n* of a layer means that both the real component Re(n*) and the imaginary component Im(n*) of the complex refractive index are being determined. The complex refractive indices and thicknesses of the formed layers—which can be accurately determined in accordance with the disclosed technologies—are used during ICE fabrication to provide feedback for adjusting the ICE fabrication in real-time or near real-time. In this manner, the systems and techniques described herein can provide consistent batch-to-batch yields, and/or improvement of batch yield for the ICE fabrication. For example, viable ICE was made on the first try deposition for 5 different ICE designs using the disclosed measurement combinations for in-situ monitoring of ICE fabrication. This is in sharp contrast to the ex-situ monitoring, which requires at least one (and most often multiple) runs for measurement purposes before producing a viable ICE design.

Details of one or more of the foregoing embodiments are described below.

(3.1) System for ICE Fabrication with Associated Measurement System Based on at Least Two In-Situ Measurement Techniques A target ICE design can be provided to an ICE fabrication system in which one or more ICEs are fabricated based on the target ICE design. Technologies for in-situ adjusting ICE fabrication based on results of at least two different types of in-situ measurements are disclosed below. A fabrication system for implementing these technologies is described first.

Figure 3:
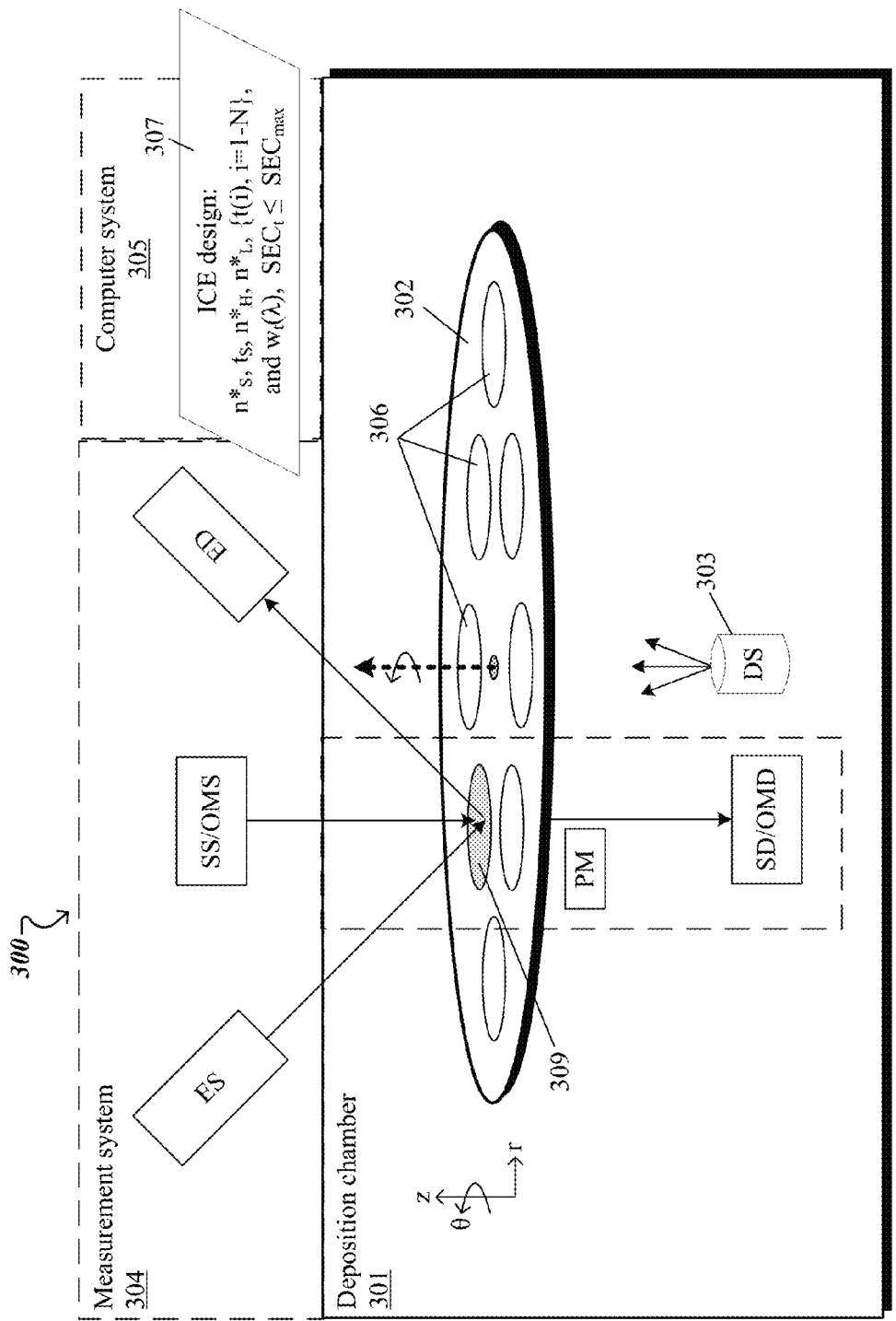
FIG. 3 shows an example of a system for ICE fabrication that has an associated measurement system used to perform a combination of measurement techniques for in-situ monitoring the ICE fabrication.

FIG. 3 shows a schematic representation of an example of an ICE fabrication system 300. The ICE fabrication system 300 includes a deposition chamber 301 to fabricate one or more ICEs 306, a measurement system 304 to measure characteristics of probe-light that interacted with formed layers of the ICE while the ICE is being fabricated, and a computer system 305 to control the fabrication of the one or more ICEs 306 based at least in part on results of the measurements.

The deposition chamber 301 includes one or more deposition sources 303 to provide materials with low complex index of refraction n*$_L$ and high complex index of refraction n*$_H$ used to form layers of the ICEs 306. Substrates on which layers of the ICEs 306 will be deposited are placed on a substrate support 302, such that the ICEs 306 are within the field of view of the deposition source(s) 303. The substrates have a thickness t$_S$ and a complex refraction index n*$_S$ specified by the ICE design 307. Various physical vapor deposition (PVD) techniques can be used to form a stack of layers of each of the ICEs 306 in accordance with a target ICE design 145 or 245, for instance. In accordance with PVD techniques, the layers of the ICE(s) are formed by condensation of a vaporized form of material(s) of the source(s) 305, while maintaining vacuum in the deposition chamber 301. One such example of PVD technique is electron beam (E-beam) deposition, in which a beam of high energy electrons is electromagnetically focused onto material(s) of the deposition source(s) 303, e.g., either Si, or $SiO_2$, to evaporate atomic species. In some cases, E-beam deposition is assisted by ions, provided by ion-sources (not shown in FIG. 3), to clean or etch the ICE substrate(s); and/or to increase the energies of the evaporated material(s), such that they are deposited onto the substrates more densely, for instance. Other examples of PVD techniques that can be used to form the stack of layers of each of the ICEs 306 are cathodic arc deposition, in which an electric arc discharged at the material(s) of the deposition source(s) 303 blasts away some into ionized vapor to be deposited onto the ICEs 306 being formed; evaporative deposition, in which material(s) included in the deposition source(s) 303 is(are) heated to a high vapor pressure by electrically resistive heating; pulsed laser deposition, in which a laser ablates material(s) from the deposition source(s) 303 into a vapor; or sputter deposition, in which a glow plasma discharge (usually localized around the deposition source(s) 303 by a magnet—not shown in FIG. 3) bombards the material(s) of the source(s) 303 sputtering some away as a vapor for subsequent deposition.

A relative orientation of and separation between the deposition source(s) 303 and the substrate support 302 are configured to provide desired deposition rate(s) and spatial uniformity across the ICEs 306 disposed on the substrate support 302. As a spatial distribution of a deposition plume provided by the deposition source(s) 303 is non-uniform along at least a first direction, the substrate support 302 is periodically moved with respect to the deposition source 303 along the first direction (e.g., rotated along an azimuthal direction "θ" about an axis that passes through the deposition source(s) 303) to obtain reproducibly uniform layer deposition of the ICEs 306 within a batch.

The measurement system 304 associated with the ICE fabrication system 300 includes multiple instruments. For example, a physical thickness monitor (e.g., a quartz crystal microbalance—not shown in FIG. 3) is used to measure one or more deposition rates, R. The measured deposition rate(s) R is/are used to control power provided to the deposition source(s) 303, its/their arrangement relative to the substrate support 302, etc. For instance, if an ICE design specifies that a $j^{th}$ layer L(j) of the N layers of an ICE is a Si layer with a target thickness t(j), a stack including the previously formed ICE layers L(1), ..., L(j−1) is exposed to a Si source—from among the deposition sources 303—for a duration $\Delta T(j)=t(j)/R_{Si}$, where the $R_{Si}$ is the measured deposition rate of the Si source. The measured deposition rate(s) R and the times used to deposit the formed layers L(1), L(2), ..., L(j−1), L(j) can be used by the computer system 305 to determine actual values of the thicknesses $t'_p(1), t'_p(2), \ldots, t'_p(j-1), t'_p(j)$ of these layers. The subscript "p" indicates that the thicknesses are determined from results of physical monitoring.

Actual complex refractive indices and thickness of the formed layers L(1), L(2), ..., L(j−1), L(j) also are determined by the computer system 305 from measurements of characteristics of probe-light that interacted with the formed layers. Note that probe-light represents any type of electromagnetic radiation having one or more probe wavelengths from an appropriate region of the electromagnetic spectrum. Such characteristics of the interacted probe-light are measured with at least two of other instruments of the measurement system 304 associated with the ICE fabrication system 300.

An example of an instrument of the measurement system 304 used to measure in-situ characteristics of the probe-light that interacted with the formed layers is an ellipsometer. The ellipsometer is used to measure, e.g., during or after forming the $j^{th}$ layer of the ICEs 306, amplitude and phase components (Ψ(j), Δ(j)) of elliptically polarized probe-light—provided by source ES—after reflection from a stack with j layers of a witness sample 309 that is being formed in the deposition chamber 301. In this case, the probe-light is provided by the source ES through a probe port of the deposition chamber 301 associated with the ellipsometer, and the reflected light is collected by a detector ED through a detector port of the deposition chamber 301 associated with the ellipsometer. Here, the measured amplitude and phase components (Ψ(j), Δ(j)) can be used by the computer system 305 to determine the (real and imaginary components of) complex refractive indices and thicknesses of each of the formed layers in the stack: $n*'_{e-Si}, n*'_{e-SiO2}, \{t'_e(1), t'_e(2), \ldots t'_e(j-1), t'_e(j)\}$. The computer system 305 makes this determination by solving Maxwell's equations for propagating the interacted probe-light through the formed layers in the stack. The subscript "e" indicates that the complex refractive indices and thicknesses are determined from results of ellipsometry.

Another example of an instrument of the measurement system 304 used to measure in-situ characteristics of the probe-light that interacted with the formed layers is an optical monitor. The optical monitor is used to measure, e.g., during or after forming the $j^{th}$ layer of the ICEs 306, change of intensity $I(j;\lambda_k)$ of a probe-light—provided by source OMS—due to transmission through the stack with j layers of a witness sample 309 that is being formed in the deposition chamber 301. Here, the probe-light has one or more "discrete" wavelengths $\{\lambda_k, k=1, 2, \ldots\}$. A discrete wavelength $\lambda_k$ includes a center wavelength $\lambda_k$ within a narrow bandwidth $\Delta\lambda_k$, e.g., ±5 nm or less; two or more wavelengths, $\lambda_1$ and $\lambda_2$, contained in the probe-light have respective bandwidths $\Delta\lambda_1$ and $\Delta\lambda_2$ that are not overlapping. The source OMS can be a continuous wave (CW) laser, for instance. In this case, the source OMS provides probe-light through a probe port of the deposition chamber 301 associated with the optical monitor, and a detector OMD collects, through a detector port of the deposition chamber 301 associated with the optical monitor, the transmitted light with an intensity $I(j;\lambda_k)$. Here, the measured change of intensity $I(j;\lambda_k)$ can be used by the computer system 305 to determine the complex refractive indices and thicknesses of each of the formed layers in the stack: $n*'_{o-Si}, n*'_{o-SiO2}, \{t'_o(1), t'_o(2), t'_o(j-1), t'_o(j)\}$. The computer system 305 makes this determination by solving Maxwell's equations for propagating the interacted probe-light through the formed layers in the stack. The subscript "o" indicates that the complex refractive indices and thicknesses are determined from results of optical monitoring.

Another example of an instrument of the measurement system 304 used to measure in-situ characteristics of the probe-light that interacted with the formed layers is a spectrometer. The spectrometer is used to measure, e.g., during or after forming the $j^{th}$ layer of the ICEs 306, a spectrum $S(j;\lambda)$ of light—provided by a source SS over a broad and typically continuous wavelength range from, $\lambda_{min}$ to $\lambda_{max}$—after transmission through the stack with j layers of a witness sample 309 that is being formed in the deposition chamber 301. In this case, the broad wavelength range source SS provides light through a probe port of the deposition chamber 301 associated with the spectrometer, and a detector SD collects the transmitted light through a detector port of the deposition chamber 301 associated with the spectrometer. Here, the measured spectrum $S(j;\lambda)$, over the wavelength range from $\lambda_{min}$ to $\lambda_{max}$, can be used by the computer system 305 to determine the complex refractive indices and thicknesses of each of the formed layers in the stack: $n'_{s\text{-}Si}$, $n'_{s\text{-}SiO2}$, $\{t'_s(1), t'_s(2), \ldots t'_s(j-1), t'_s(j)\}$. The computer system 305 makes this determination by solving Maxwell's equations for propagating the interacted probe-light through the formed layers in the stack. The subscript "s" indicates that the complex refractive indices and thicknesses are determined from results of spectroscopy.

In accordance with the disclosed technologies, the formed layers of any one or more of the current instances of the ICEs 306 can be used as a witness sample by the measurement system 304 to monitor ICE layer deposition in the deposition chamber 301. Here, the witness sample 309 is placed on the substrate support 302 adjacent or in between the one or more of the ICEs 306 being fabricated in the deposition chamber 301, so it moves with respect to the deposition source 303 along a path similar to the paths of the ICEs 306. In this manner, the witness sample 309 experiences similar deposition conditions in the deposition chamber 301 as the ICEs 306, so properties of the witness sample 309 (e.g., complex refractive indices and thicknesses of layers of the witness sample) are similar to the corresponding properties of the fabricated ICEs 306. Conventionally, a witness sample is often placed relative to a deposition source in locations of a deposition chamber that are easy to measure, but typically such locations of the witness sample can be substantially different from locations where ICEs are placed in the deposition chamber. For example, the witness sample may be conventionally placed at the center of the deposition chamber or to one side thereof. In such cases, the witness sample is at rest relative to the deposition source, while the ICEs—placed on a substrate support—rotate about the deposition source. Hence, the witness sample experiences different deposition conditions in the deposition chamber from the ones experienced by the ICEs. As such, conventional placement of a witness sample may result in properties of the witness sample that are dissimilar from properties of the fabricated ICEs.

In some implementations, e.g., for in-situ ellipsometry measurements, a substrate of the witness sample 309 may be treated (e.g., its back surface can be roughened or coated) to provide improved reflection with respect to an untreated substrate of the other ICEs 306. In some implementations, an area of the witness sample 309 may be larger than the area of the other ICEs 306, e.g., "K" times larger. In such cases, at the end of the ICE fabrication, the witness sample 309 may be cut into (up to) K pieces to use the resulting K ICEs—along with the other ICEs 306 from the same fabrication batch—in logging tools. Such witness samples 309 that have differently treated substrate or different size from the ICEs 306 can be disposed at predetermined or random locations on the substrate support 302 among the other ICEs 306. In some implementations, any one or more of the ICEs 306 (without having differently treated substrates or different sizes) can be used as the one or more witness samples 309.

In some implementations, the witness sample 309 is at rest with respect to an instrument (e.g., ellipsometer, optical monitor, or spectrometer) of the measurement system 304 when the characteristics of the interacted light are measured. Here, deposition of a layer L(j) is interrupted or completed prior to performing the measurement. For some of the layers of an ICE design, the instrument measures in-situ the characteristics of interacted probe-light after the layer L(j) has been deposited to its full target thickness t(j), or equivalently, when deposition of the layer L(j) is completed. For some of the layers of the ICE design, the instrument measures the characteristics of the interacted probe-light during the deposition of the layer L(j). For example, such a measurement can be taken when the layer L(j) has been deposited to a fraction of its target thickness f*t(j), e.g., where f=50%, 80%, 90%, 95%, etc.

In other implementations, the witness sample 309 moves with respect to an instrument (e.g., ellipsometer, optical monitor, or spectrometer) of the measurement system 304, e.g., rotates about an azimuthal axis of the substrate support 302 along with the other ICEs 306, when the characteristics of the interacted probe-light are measured. Here, deposition of the layer L(j) may—but need not be—interrupted or completed prior to performing the measurement. For some of the layers of the ICE design, measurements of characteristics of the interacted probe-light can be taken continuously for the entire duration $\Delta T(j)$ of the deposition of the layer L(j), or at least for portions thereof, e.g., last 50%, 20%, 10% of the entire duration $\Delta T(j)$. In these implementations, a signal of interest (e.g., probe-light polarization modified by reflection off the witness sample 309 for ellipsometry; change of intensity of probe-light transmitted through the witness sample 309 of optical monitoring; or probe-light spectrum modified by transmission through the witness sample 309 for spectroscopy) is collected by the instrument's detector (ED for the ellipsometer, OMD for optical monitor, or SD for the spectrometer) during the time when the moving witness sample 309 is illuminated by the probe-light. For example, as the movement of the witness sample 309 is periodic, the signal of interest is averaged over a number of periods of the periodic motion, for instance over 5 periods. As another example, a number $M \geq 2$ of witness samples along the direction of motion can be successively illuminated by the probe-light over each period of the periodic motion. Here, the signal of interest is averaged over the M witness samples. Whether for a single witness sample or for multiple witness samples, no signal is collected, by the instrument's detector for the remainder of a period of the periodic motion, when the probe-light does not illuminate the witness sample(s) 309.

One complication with measurements of near-infrared (NIR) or mid-infrared (MIR) transmission spectra is that stray light emanating from any warm (e.g., a blackbody) surface inside the deposition chamber 301 enters the spectrometer's detector SD and interferes with the measurement. To avoid these complications, the spectrometer of the measurement system 304 is chosen to be a single-shot (non-scanning) spectrometer to perform fast spectroscopy. Here, the detector SD of the single-shot spectrometer can be a photodiode array or a CCD array. In this case, a transmission spectrum of the formed layers is collected from and averaged over all the ICEs 306 that are illuminated by the probe-light during a period of the periodic motion of the substrate support 302. In this manner, as the substrate support 302 moves periodically, the probe of the spectrometer alternately goes through an ICE 306, and then the probe is blocked by the physical substrate support 302 until the next ICE enters the probe. A spectrum corresponding to the formed layers of the ICEs 306 is collected by the detector SD when the probe-light illuminates any of the ICEs 306, and a background spectrum is collected by the detector SD when the probe illuminates adjacent to (in between) the ICEs 306 and it is physically blocked from reaching the detector SD. In addition, at least one reference spectrum (also referred to as a baseline spectrum) is collected during the period of the periodic motion when the probe passes through an aperture of the substrate support 302 without passing through a witness sample 309 and without being blocked by the substrate support 302. The reference spectrum is used by the computer system 305 to subtract (or normalize) from the spectrum associated with the deposited layers (1) temporal and/or spectral variations of the probe-light and (2) a spectral response of the detector SD over the wavelength range $[\lambda_{min},\lambda_{max}]$ of the probe-light. Moreover, the background spectrum is used to compensate (or zero out) much of spectral contributions of the stray light both from the reference spectrum and from the spectrum associated with the deposited layers. The foregoing allows for accurate baseline and background corrections and thus enables recording of an accurate spectrum associated with the deposited layers of the ICEs 306.

In some implementations, the measurement system 304 includes only the ellipsometer and the optical monitor described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; and (2) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309.

In other implementations, the measurement system 304 includes only the ellipsometer and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309, and (2) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

In some other implementations, the measurement system 304 includes only the spectrometer and the optical monitor described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309; and (2) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309.

In yet other implementations, the measurement system 304 includes only the ellipsometer, the optical monitor and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; (2) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309; and (3) complex refractive indices $n^{*'}_{s-H}$, $n^*_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

In yet other implementations, the measurement system 304 includes only the ellipsometer and the physical monitor described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; and (2) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306.

In yet other implementations, the measurement system 304 includes only the physical monitor and the optical monitor described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306; and (2) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309.

In yet other implementations, the measurement system 304 includes only the physical monitor and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306; and (2) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

In yet other implementations, the measurement system 304 includes only the ellipsometer, the optical monitor and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; (2) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309; and (3) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

In yet other implementations, the measurement system 304 includes only the ellipsometer, the physical monitor and the optical monitor described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; (2) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306; and (3) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309.

In yet other implementations, the measurement system 304 includes only the ellipsometer, the physical monitor and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; (2) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306; and (3) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

In yet other implementations, the measurement system 304 includes the physical monitor, the optical monitor and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306; (2) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309; and (3) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

In yet other implementations, the measurement system 304 includes the ellipsometer, the physical monitor the optical monitor and the spectrometer described above. Here, complex refractive indices $n^{*'}_H$, $n^{*'}_L$ and thicknesses $\{t'(1), \ldots, t'(j)\}$ of the deposited layers $L(1), \ldots, L(j)$ of the ICEs 306 are obtained by weighting the corresponding (1) complex refractive indices $n^{*'}_{e-H}$, $n^{*'}_{e-L}$ and thicknesses $\{t'_e(1), \ldots, t'_e(j)\}$ of the deposited layers $L(1), \ldots, L(j)$ of the ICEs 306 determined from results of the ellipsometry measurements of amplitude and phase components $(\Psi(j), \Delta(j))$ of elliptically polarized probe-light modified by reflection off the witness sample 309; (2) thicknesses $\{t'_p(1), \ldots, t'_p(j)\}$ of the deposited layers $L(1), \ldots, L(j)$ of the ICEs 306 determined from results of the physical monitoring measurements of one or more deposition rates used to deposed the formed layers of the ICEs 306; (3) complex refractive indices $n^{*'}_{o-H}$, $n^{*'}_{o-L}$ and thicknesses $\{t'_o(1), \ldots, t'_o(j)\}$ of the deposited layers $L(1), \ldots, L(j)$ of the ICEs 306 determined from results of the optical monitoring measurements of change of intensity $I(j;\lambda_k)$ of probe-light transmitted through the witness sample 309; and (4) complex refractive indices $n^{*'}_{s-H}$, $n^{*'}_{s-L}$ and thicknesses $\{t'_s(1), \ldots, t'_s(j)\}$ of the deposited layers $L(1), \ldots, L(j)$ of the ICEs 306 determined from results of the spectroscopic measurements of probe-light spectrum $S(j;\lambda)$ modified by transmission through the witness sample 309.

The computer system 305 includes one or more hardware processors and memory. The memory encodes instructions that, when executed by the one or more hardware processors, cause the fabrication system 300 to perform processes for fabricating the ICEs 306. Examples of such processes are described below in connection with FIGS. 4A-4B. The computer system 305 also includes or is communicatively coupled with a storage system that stores one or more ICE designs 307, aspects of the deposition capability, and other information. The stored ICE designs can be organized in design libraries by a variety of criteria, such as ICE designs used to fabricate ICEs for determining values of a particular characteristic over many substances (e.g. the GOR ratio in crude oil, refined hydrocarbons, mud, etc.), or ICE designs used to fabricate ICEs for determining values of many characteristics of a given substance (e.g., viscosity, GOR, density, etc., of crude oil.) In this manner, upon receipt of an instruction to fabricate an ICE for measuring a given characteristic of a substance, the computer system 305 accesses such a design library and retrieves an appropriate ICE design 307 that is associated with the given characteristic of the substance.

The retrieved ICE design 307 includes specification of a substrate and a total number N of layers to be formed in the deposition chamber 301 on the substrate; specification of a complex refractive index $n^*_S$ of a material of the substrate, a high complex refractive index $n^*_H$ and a low complex refractive index $n^*_L$ of materials (e.g., Si and $SiO_2$) to form the N layers with adjacent layers having different complex refractive indices; and specification of target thicknesses $\{t_S, t(k), k=1-N\}$ of the substrate and the N layers. Implicitly or explicitly, the ICE design 307 also can include specification of a target optical spectrum $w_t(\lambda)$ associated with the given characteristic; and specification of a target $SEC_t$ representing expected performance of an ICE associated with the retrieved ICE design 307. The foregoing items of the retrieved ICE design 307 were determined, prior to fabricating the ICEs 306, in accordance with the ICE design process 200 described above in connection with FIG. 2. In some implementations, the ICE design 307 can include indication of maximum allowed $SEC_{max}$ caused by fabrication errors. Figures of merit other than the target $SEC_t$ can be included in the retrieved ICE design 307, e.g., SEP, the ICE sensitivity, etc.

The complex refractive indices and target thicknesses $\{t(k), k=1\text{-}N\}$ of the N layers, as specified by the retrieved ICE design 307, are used by the computer system 305, in conjunction with aspects of deposition capability of the ICE fab system 300, to control deposition rate(s) of the deposition source(s) 303 and respective deposition times for forming the ICE layers. While forming the ICE layers, the computer system 305 instructs the measurement system 304 associated with the ICE fabrication system 300 to measure characteristics of probe-light that interacted with formed layers of the ICE by performing at least two different types of in-situ measurements. The measured characteristics of the probe-light that interacted with the formed layers of the ICE are used by the computer system 305 to determine complex refractive indices and thicknesses of the formed layers of the ICE. If necessary, the computer system 305 then instructs the ICE fabrication system 300 to adjust the forming of layers remaining to be formed based on the determined complex refractive indices and thicknesses of the formed layers of the ICE.

Figure 4A:
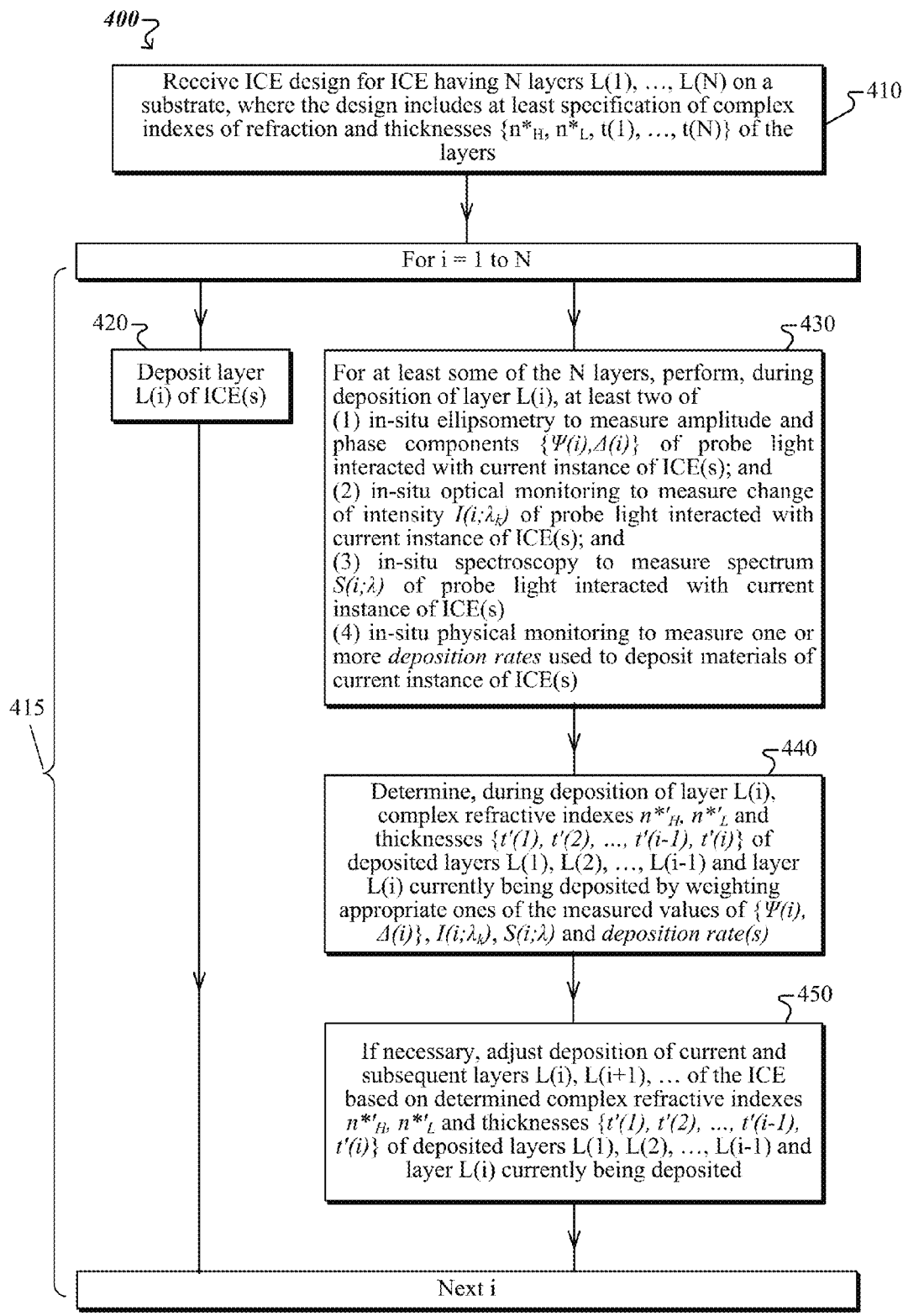
FIGS. 4A-4B are flowcharts showing aspects of an example of an ICE fabrication that uses a combination of measurement techniques for in-situ monitoring of the ICE fabrication.

(3.2) Real-Time and Near Real-Time Adjusting of ICE Fabrication Based on Results from at Least Two In-Situ Measurement Techniques FIG. 4A is a flow chart of an example of an ICE fabrication process 400 for fabricating ICEs that uses a combination of measurement techniques for in-situ monitoring of the ICE fabrication. The process 400 can be implemented in conjunction with the ICE fabrication system 300 to adjust ICE fabrication. In such a context, the process 400 can be implemented as instructions encoded in the memory of the computer system 305, such that execution of the instructions, by the one or more hardware processors of the computer system 305, causes the ICE fabrication system 300 to perform the following operations.

At 410, an ICE design is received. The received ICE design includes specification of a substrate and N layers L(1), L(2), ..., L(N), each having a different complex refractive index from its adjacent layers, and specification of target complex refractive indices and thicknesses $t_S$, $t(1), t(2), \ldots, t(N)$. In this manner, an ICE fabricated in accordance with the received ICE design selectively weights, when operated, light in at least a portion of a wavelength range by differing amounts. The differing amounts weighted over the wavelength range correspond to a target optical spectrum $w_t(\lambda)$ of the ICE and are related to a characteristic of a sample. For example, a design process for determining the specified (1) substrate and number N of layers of the ICE, each having a different complex refractive index from its adjacent layers, and (2) complex refractive indices and thicknesses of the substrate and the N layers that correspond to the target optical spectrum $w_t(\lambda)$ of the ICE is described above in connection with FIG. 2. In some implementations, the received ICE design also can include $SEC_t$ as an indication of a target performance of the ICE. The target performance represents an accuracy with which the ICE predicts, when operated, known values of the characteristic corresponding to validation spectra of the sample. Here, predicted values of the characteristic are obtained when the validation spectra weighted by the ICE are respectively integrated. In some implementations, the received ICE design also can include indication of maximum allowed $SEC_{max}$ caused by fabrication errors.

Loop 415 is used to fabricate one or more ICEs based on the received ICE design. Each iteration "i" of the loop 415 is used to form a layer L(i) of a total number N of layers. Here, the total number N of layers can be either specified in the received ICE design or updated during the ICE fabrication. Updates to the received ICE design are performed when necessary for preventing performance of the fabricated ICE to degrade under a threshold value.

At 420, the layer L(i) is formed to a target thickness t(i). The target thickness t(i) of the layer L(i) can be specified by the received ICE design or updated based on optimization(s) carried out after forming previous one or more of the layers of the ICE. For some of the layers of the ICE, a deposition source having a deposition rate R is used for a total time duration $\Delta T(i)=t(i)/R$ to deposit the layer L(i) to its target thickness as part of a single deposition step. Other layers are deposited to the target thickness t(i) using multiple deposition steps by discretely or continuously forming respective sub-layers of the layer L(i). Here, the deposition rate used for depositing each of the sub-layers can be the same or different from each other. In the case when the deposition rates for forming the sub-layers are different, the last few sub-layers of the layer L(i) can be formed using slower rates than the ones used for forming the first few sub-layers of the layer L(i).

At 430, while the layer L(i) is being formed, at least two in-situ measurements are performed. In-situ optical measurements are implemented to determine changes in characteristics of a probe-light due to its interaction with the layer currently being formed and the previously formed layers. In the example illustrated in FIG. 3, the in-situ optical measurements performed using the measurement system 304 include at least two of (1) in-situ ellipsometry to measure amplitude and phase components $\{\Psi(i),\Delta(i)\}$ of probe-light interacted with a current instance of the ICE(s), (2) in-situ optical monitoring to measure change of intensity $I(i;\lambda_k)$ of probe-light interacted with the current instance of ICE(s), and (3) in-situ spectroscopy to measure a spectrum $S(i;\lambda)$ of probe-light interacted with the current instance of ICE(s). In-situ physical measurements, e.g., physical monitoring based on a quartz microbalance as illustrated in FIG. 3, are implemented to determine one or more deposition rates used to deposit respective materials of the current instance of the ICE(s).

For some of the layers of the received ICE design, the at least two in-situ measurements can be skipped altogether. For some other layers, the at least two in-situ measurements are carried out continuously during the deposition of a layer L(i), in some implementations. In other implementations, the at least two in-situ measurements are taken a finite number of times during the deposition of the layer L(i). In the latter case, the finite number of times includes times when at least some of the sub-layers of the layer L(i) are completed. In some other implementations, some of the at least two in-situ measurements are performed continuously and the remaining ones are performed a finite number of times during the deposition of the layer L(i).

In some implementations, a combination of two, three or four in-situ measurements from among the ellipsometry, physical monitoring, optical monitoring and spectroscopy are performed for each of at least some of the layers of the ICE.

Results of the combination of the two, three or four in-situ measurements are weighted using weights proportional to an accuracy associated with each of the in-situ measurements as a function of the number of deposited layers L(1), L(2), . . . , L(i).

Examples of such a combination of two in-situ measurements performed for each of at least some of the layers of the ICE are: ellipsometry to measure amplitude and phase components of the probe-light that interacted with the current instance of the ICE, and physical monitoring to measure one or more deposition rates used to deposit respective materials of the current instance of the ICE; ellipsometry to measure the amplitude and phase components, and optical monitoring to measure change of intensity of the probe-light that interacted with the current instance of the ICE; ellipsometry to measure the amplitude and phase components, and spectroscopy to measure a spectrum of the probe-light that interacted with the current instance of the ICE; physical monitoring to measure the one or more deposition rates, and optical monitoring to measure the change of intensity; physical monitoring to measure the one or more deposition rates, and spectroscopy to measure the spectrum; optical monitoring to measure the change of intensity, and spectroscopy to measure the spectrum.

Examples of such a combination of three in-situ measurements performed for each of at least some of the layers of the ICE are: ellipsometry to measure amplitude and phase components of the probe-light that interacted with the current instance of the ICE, physical monitoring to measure one or more deposition rates used to deposit respective materials of the current instance of the ICE, and optical monitoring to measure change of intensity of the probe-light that interacted with the current instance of the ICE; ellipsometry to measure the amplitude and phase components, physical monitoring to measure the one or more deposition rates, and spectroscopy to measure a spectrum of the probe-light that interacted with the current instance of the ICE; ellipsometry to measure the amplitude and phase components, optical monitoring to measure the change of intensity, and spectroscopy to measure the spectrum; physical monitoring to measure the amplitude and phase components, optical monitoring to measure the one or more deposition rates, and spectroscopy to measure the spectrum.

In some implementations, only one of a sequence of four in-situ measurements is performed, at 430, while the layer L(i) is being formed, at 420. The sequence order in which the four in-situ measurements are performed is established based on an accuracy associated with each of the in-situ measurements as a function of the number of deposited layers L(1), L(2), . . . , L(i). For example, when fewer than a first number "j" of layers of the ICE have been formed (i<j), in-situ ellipsometry is performed while the layer L(i) is being formed to measure amplitude and phase components of the probe-light that interacted with the current instance of the ICE. When at least the first number "j" of layers but fewer than a second number "k" of layers of the ICE have been formed (j≤i<k), in-situ physical monitoring is performed to measure one or more deposition rates used to deposit respective materials of the current instance of the ICE. When at least the second number "k" of layers but fewer than a third number "p" of layers of the ICE have been formed (k≤i<p), in-situ optical monitoring is performed to measure change of intensity of the probe-light that interacted with the current instance of the ICE. And, when at least the third number "p" of layers have been formed (p≤i), in-situ spectroscopy is performed to measure a spectrum of the probe-light that interacted with the current instance of the ICE.

In other implementations, only one of a sequence of three in-situ measurements is performed, at 430, while the layer L(i) is being formed, at 420. The sequence order in which the three in-situ measurements are performed is established based on an accuracy associated with each of the in-situ measurements as a function of the number of deposited layers L(1), L(2), . . . , L(i). For example, when fewer than a first number "j" of layers of the ICE have been formed (i<j), in-situ ellipsometry is performed while the layer L(i) is being formed to measure amplitude and phase components of the probe-light that interacted with the current instance of the ICE. When at least the first number "j" of layers but fewer than a second number "k" of layers of the ICE have been formed (j≤i<k), in-situ optical monitoring is performed to measure change of intensity of the probe-light that interacted with the current instance of the ICE. And, when at least the second number "k" of layers have been formed (k≤i), in-situ spectroscopy is performed to measure a spectrum of the probe-light that interacted with the current instance of the ICE. As another example, when fewer than a first number "j" of layers of the ICE have been formed (i<j), in-situ ellipsometry is performed while the layer L(i) is being formed to measure amplitude and phase components of the probe-light that interacted with the current instance of the ICE. When at least the first number "j" of layers but fewer than a second number "k" of layers of the ICE have been formed (j≤i<k), in-situ physical monitoring is performed to measure one or more deposition rates used to deposit respective materials of the current instance of the ICE. And, when at least the second number "k" of layers have been formed (k≤i), in-situ spectroscopy is performed to measure a spectrum of the probe-light that interacted with the current instance of the ICE. As yet another example, when fewer than a first number "j" of layers of the ICE have been formed (i<j), in-situ ellipsometry is performed while the layer L(i) is being formed to measure amplitude and phase components of the probe-light that interacted with the current instance of the ICE. When at least the first number "j" of layers but fewer than a second number "k" of layers of the ICE have been formed (j≤i<k), in-situ physical monitoring is performed to measure one or more deposition rates used to deposit respective materials of the current instance of the ICE. And, when at least the second number "k" of layers have been formed (k≤i), in-situ optical monitoring is performed to measure change of intensity of the probe-light that interacted with the current instance of the ICE. As yet another example, when fewer than a first number "j" of layers of the ICE have been formed (i<j), in-situ physical monitoring is performed to measure one or more deposition rates used to deposit respective materials of the current instance of the ICE. When at least the first number "j" of layers but fewer than a second number "k" of layers of the ICE have been formed (j≤i<k), in-situ optical monitoring is performed to measure change of intensity of the probe-light that interacted with the current instance of the ICE. And, when at least the second number "k" of layers have been formed (k≤i), in-situ spectroscopy is performed to measure a spectrum of the probe-light that interacted with the current instance of the ICE.

In some other implementations, only one of a sequence of two in-situ optical measurements is performed, at 430, while the layer L(i) is being formed, at 420. The sequence order in which the two in-situ measurements are performed is established based on an accuracy associated with each of the in-situ measurements as a function of the number of deposited layers L(1), L(2), . . . , L(i). For example, when fewer than a first number "j" of layers of the ICE have been formed (i<j), in-situ ellipsometry is performed while the layer L(i) is being formed to measure amplitude and phase components of the probe-light that interacted with the current instance of the ICE. And, when at least the first number "j" of layers have been formed (j≤i), in-situ spectroscopy is performed to measure a spectrum of the probe-light that interacted with the current instance of the ICE. As another example, when fewer than a first number "j" of layers of the ICE have been formed (i<j), in-situ optical monitoring is performed while the layer L(i) is being formed to measure change of intensity of the probe-light that interacted with the current instance of the ICE. And, when at least the first number "j" of layers have been formed (j≤i), in-situ spectroscopy is performed to measure a spectrum of the probe-light that interacted with the current instance of the ICE. As yet another example, when fewer than a first number "j" of layers of the ICE have been formed (i<j), in-situ ellipsometry is performed while the layer L(i) is being formed to measure amplitude and phase components of the probe-light that interacted with the current instance of the ICE. And, when at least the first number "j" of layers have been formed (j≤i), in-situ optical monitoring is performed to measure change of intensity of the probe-light that interacted with the current instance of the ICE. As yet another example, in-situ ellipsometry is performed while the layer L(i) is being formed to measure amplitude and phase components of the probe-light that interacted with the current instance of the ICE. And, when at least the first number "j" of layers have been formed (j≤i), in-situ physical monitoring is performed to measure one or more deposition rates used to deposit respective materials of the current instance of the ICE. As yet another example, in-situ optical monitoring is performed while the layer L(i) is being formed to measure change of intensity of the probe-light that interacted with the current instance of the ICE. And, when at least the first number "j" of layers have been formed (j≤i), in-situ physical monitoring is performed to measure one or more deposition rates used to deposit respective materials of the current instance of the ICE. As yet another example, when fewer than a first number "j" of layers of the ICE have been formed (i<j), in-situ physical monitoring is performed to measure one or more deposition rates used to deposit respective materials of the current instance of the ICE. And, when at least the first number "j" of layers have been formed (j≤i), in-situ spectroscopy is performed to measure a spectrum of the probe-light that interacted with the current instance of the ICE.

At 440, complex refractive indices $n^{*\prime}_H$ and $n^{*\prime}_L$ and thicknesses $t'(1), t'(2), \ldots, t'(i-1), t'(i)$ of the layers $L(1), L(2), \ldots, L(i-1)$ formed in previous iterations of the loop 415 and the layer $L(i)$ that is currently being formed are determined by weighting appropriate ones of the measured values of (1) amplitude and phase components $\{\Psi(i), \Delta(i)\}$ of probe-light interacted with a current instance of the ICE(s), (2) change of intensity $I(i;\lambda_k)$ of probe-light interacted with the current instance of ICE(s), (3) a spectrum $S(i;\lambda)$ of probe-light interacted with the current instance of ICE(s) measured at 430, and (4) one or more deposition rates used to deposit materials of the current instance of ICE(s) measured at 430.

Figure 4B:
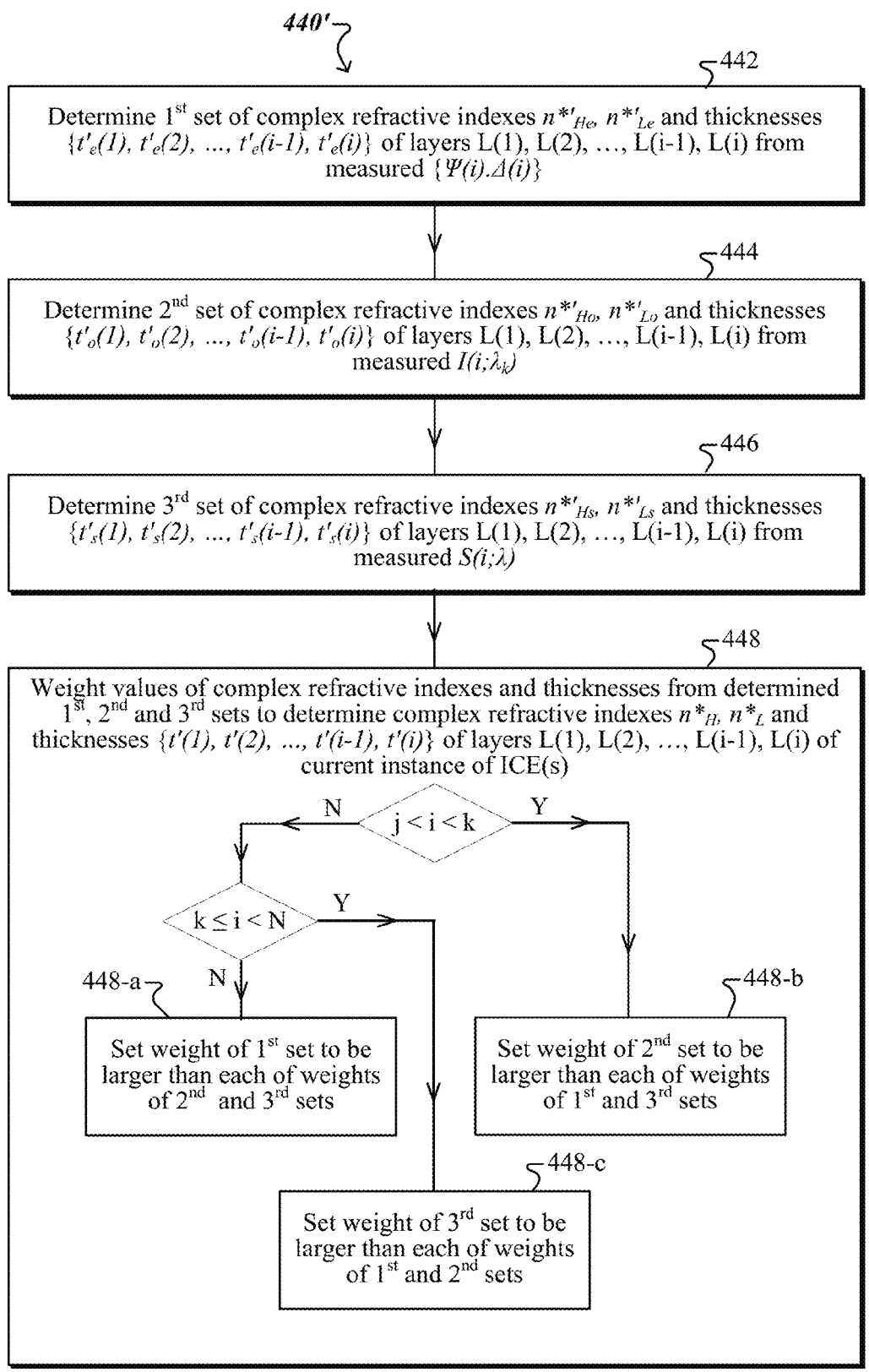

FIG. 4B is a flow chart of an example of a process 440' for determining the complex refractive indices $n^{*\prime}_H$ and $n^{*\prime}_L$ and thicknesses $t'(1), t'(2), \ldots, t'(i-1), t'(i)$ of the layers $L(1), L(2), \ldots, L(i-1)$ formed in previous iterations of the loop 415 and the layer $L(i)$ that is currently being formed based on results of three in-situ optical measurements of the four in-situ measurements performed during deposition of the layer $L(i)$.

At 442, a first set of complex refractive indices $n^{*\prime}_{e-H}$, $n^{*\prime}_{e-L}$ and thicknesses $\{t'_e(1), \ldots, t'_e(i)\}$ of the layers $L(1), \ldots, L(i)$ of a current instance of ICE(s) are determined from results of in-situ ellipsometry measurements of amplitude and phase components $(\Psi, \Delta)$ of elliptically polarized probe-light modified by reflection off the layers $L(1), \ldots, L(i)$ of the current instance of ICE(s). At 444, a second set of complex refractive indices $n^{*\prime}_{o-H}$, $n^{*\prime}_{o-L}$ and thicknesses $\{t'_o(1), \ldots, t'_o(j)\}$ of the layers $L(1), \ldots, L(j)$ of the current instance of ICE(s) are determined from results of in-situ optical monitoring measurements of change of intensity of probe-light transmitted through the layers $L(1), \ldots, L(i)$ of the current instance of ICE(s). At 446, a third set of complex refractive indices $n^{*\prime}_{s-H}$, $n^{*\prime}_{s-L}$ and thicknesses $\{t'_s(1), \ldots, t'_s(j)\}$ of the layers $L(1), \ldots, L(j)$ of the ICEs are determined from results of in-situ spectroscopy measurements of probe-light spectrum modified by transmission through the layers $L(1), \ldots, L(i)$ of the current instance of ICE(s).

At 448, values of complex refractive indices and thicknesses from the determined first, second and third sets are weighted to determine complex refractive indices $n^{*\prime}_H$, $n^{*\prime}_L$ and thicknesses $\{t'(1), t'(2), \ldots, t'(i-1), t'(i)\}$ of layers $L(1), L(2), \ldots, L(i-1), L(i)$ of the current instance of ICE(s). In this manner, the complex refractive indices and thicknesses can be determined in the following manner:

$$n^{*\prime}_H = w_e \cdot n^{*\prime}_{e-H} + w_o \cdot n^{*\prime}_{o-H} + w_s \cdot n^{*\prime}_{s-H}, \quad (1)$$

$$n^{*\prime}_L = w_e \cdot n^{*\prime}_{e-L} + w_o \cdot n^{*\prime}_{o-L} + W_s \cdot n^{*\prime}_{s-L}, \quad (2)$$

$$t'(i) = w_e \cdot t'_e(i) + w_o \cdot t'_o(i) + w_s \cdot t'_s(i), \text{ where } i=1-N. \quad (3)$$

In equations (1), (2) and (3), a weight $w_e$ is used to weight results of the ellipsometry measurements, a weight $w_o$ is used to weight results of the optical monitoring measurements, and a weight $w_s$ is used to weight results of the spectroscopy measurements. In some implementations, the weights of the three in-situ optical measurements are equal: $w_e = w_o = w_s = 1/3$. In other implementations, the weights of the three in-situ optical measurements are proportional to an accuracy associated with each of the in-situ optical measurements as a function of the number of deposited layers $L(1), L(2), \ldots, L(i)$. At 448-a, for the first "j" layers when i<j, the weight $w_e$ used to weight the first set of complex refractive indices $n^{*\prime}_{e-H}$, $n^{*\prime}_{e-L}$ and thicknesses $\{t'_e(1), \ldots, t'_e(i)\}$ determined based on results of ellipsometry measurements is larger than each of the weights $w_o$ and $w_s$ associated with the second and third sets, respectively. For example, for the first two layers (j=2), the following weights may be used $w_e=0.8$, $w_o=0.15$ and $w_s=0.05$. At 448-b, for a stack with an intermediary number of layers when j<i≤k, the weight $w_o$ used to weight the second set of complex refractive indices $n^{*\prime}_{o-H}$, $n^{*\prime}_{o-L}$ and thicknesses $\{t'_o(1), \ldots, t'_o(i)\}$ determined based on results of optical monitoring measurements is larger than each of the weights $w_e$ and $w_s$ associated with the first and third sets, respectively. For example, for stacks having between 3-6 layers (j=2, k=6), the following weights may be used $w_o=0.6$, $w_e=0.2$ and $w_s=0.2$. At 448-c, for a stack with a larger number of layers when k<i, the weight $w_s$ used to weight the third set of complex refractive indices $n^{*\prime}_{s-H}$, $n^{*\prime}_{s-L}$ and thicknesses $\{t'_s(1), \ldots, t'_s(i)\}$ determined based on results of spectrometry measurements is larger than each of the weights $w_e$ and $w_o$ associated with the first and second sets, respectively. For example, for stacks having more than 6 layers (k=6), the following weights may be used $w_s=0.9$, $w_e=0.02$ and $w_o=0.08$.

In this example, the complex refractive indices $n^{*\prime}_H$ and $n^{*\prime}_L$ and thicknesses $t'(1), t'(2), \ldots, t'(i-1), t'(i)$ of the layers $L(1), L(2), \ldots, L(i-1)$ formed in previous iterations of the loop 415 and the layer $L(i)$ that is currently being formed are determined based on results of three in-situ ellipsometry, optical monitoring and spectroscopy performed during deposition of the layer $L(i)$.

In some implementations, the only in-situ optical measurements performed during deposition of the layer L(i) are (1) in-situ ellipsometry to measure amplitude and phase components of the probe-light that interacted with the current instance of the ICE and (2) in-situ spectroscopy to measure a spectrum of the probe-light that interacted with the current instance of the ICE. Here, determining the complex refractive indices and thicknesses of the formed layers of the ICE includes weighting values of the measured amplitude and phase components and the measured spectrum, such that the weights of the corresponding in-situ optical measurements are proportional to an accuracy associated with each of the in-situ measurements as a function of the number of deposited layers L(1), L(2), . . . , L(i). When fewer than a first number "j" of layers of the ICE have been formed (i<j), a weight $w_e$ of the amplitude component and phase component values measured through ellipsometry is set to be larger than a weight $w_s$ of the spectrum measured through spectroscopy, $w_e > w_s$. And, when at least the first number "j" of layers have been formed (j≤i), a weight $w_s$ of the spectrum measured through spectroscopy is set to be equal to or larger than a weight $w_e$ of the amplitude component and phase component values measured through ellipsometry $w_e \le w_s$. In some cases, the weight $w_s$ of the spectrum measured through spectroscopy is set to be larger than the weight $w_e$ of the amplitude component and phase component values measured through ellipsometry, $w_e < w_s$, when more than a second number "k" of layers have been formed (j<k<i).

In other implementations, the only in-situ optical measurements performed during deposition of the layer L(i) are (1) in-situ ellipsometry to measure amplitude and phase components of the probe-light that interacted with the current instance of the ICE and (2) in-situ optical monitoring to measure change of intensity of the probe-light that interacted with the formed layers of the ICE. Here, determining the complex refractive indices and thicknesses of the formed layers of the ICE includes weighting values of the measured amplitude and phase components and the measured change of intensity, such that the weights of the corresponding in-situ optical measurements are proportional to an accuracy associated with each of the in-situ measurements as a function of the number of deposited layers L(1), L(2), . . . , L(i). When fewer than a first number "j" of layers of the ICE have been formed (i<j), a weight $w_e$ of the amplitude component and phase component values measured through ellipsometry is set to be larger than a weight $w_o$ of the change of intensity measured through optical monitoring, $w_e > w_o$. And, when at least the first number "j" of layers have been formed (j≤i), a weight $w_o$ of the change of intensity measured through optical monitoring is set to be equal to or larger than a weight $w_e$ of the amplitude component and phase component values measured through ellipsometry $w_e \le w_o$. In some cases, the weight $w_o$ of the change of intensity measured through optical monitoring is set to be larger than the weight $w_e$ of the amplitude component and phase component values measured through ellipsometry, $w_e < w_o$, when more than a second number "k" of layers have been formed (j<k<i).

In some other implementations, the only in-situ optical measurements performed during deposition of the layer L(i) are (1) in-situ optical monitoring to measure change of intensity of the probe-light that interacted with the current instance of the ICE and (2) in-situ spectroscopy to measure a spectrum of the probe-light that interacted with the current instance of the ICE. Here, determining the complex refractive indices and thicknesses of the formed layers of the ICE includes weighting values of the measured change of intensity and the measured spectrum, such that the weights of the corresponding in-situ optical measurements are proportional to an accuracy associated with each of the in-situ measurements as a function of the number of deposited layers L(1), L(2), . . . , L(i). When fewer than a first number "j" of layers of the ICE have been formed (i<j), a weight $w_o$ of the change of intensity value measured through optical monitoring is set to be larger than a weight $w_s$ of the spectrum measured through spectroscopy, $w_o > w_s$. And, when at least the first number "j" of layers have been formed (j≤i), a weight $w_s$ of the spectrum measured through spectroscopy is set to be equal to or larger than a weight $w_o$ of the change of intensity value measured through optical monitoring $w_o \le w_s$. In some cases, the weight $w_s$ of the spectrum measured through spectroscopy is set to be larger than the weight $w_o$ of the change of intensity value measured through optical monitoring, $w_o < w_s$, when more than a second number "k" of layers have been formed (j<k<i).

Referring again to FIG. 4A, at 440, complex refractive indices $n^{*'}_H$ and $n^{*'}_L$ and thicknesses t'(1), t'(2), . . . , t'(i−1), t'(i) of the layers L(1), L(2), . . . , L(i−1) formed in previous iterations of the loop 415 and the layer L(i) that is currently being formed are determined by weighting the measured values of (1) amplitude and phase components {Ψ(i),Δ(i)} of probe-light interacted with a current instance of the ICE(s), (2) one or more deposition rates used to deposit respective materials of the current instance of the ICE(s), (3) change of intensity $I(i;\lambda_k)$ of probe-light interacted with the current instance of ICE(s), and (4) a spectrum S(i;λ) of probe-light interacted with the current instance of ICE(s) measured at 430.

For example, a first set of complex refractive indices $n^{*'}_{e-H}$, $n^{*'}_{e-L}$ and thicknesses $\{t'_e(1), \ldots, t'_e(i)\}$ of the layers L(1), . . . , L(i) of a current instance of ICE(s) are determined from results of in-situ ellipsometry measurements of amplitude and phase components (Ψ, Δ) of elliptically polarized probe-light modified by reflection off the layers L(1), . . . , L(i) of the current instance of ICE(s). A second set of thicknesses $\{t'_p(1), \ldots, t'_p(j)\}$ of the layers L(1), . . . , L(j) of the current instance of ICE(s) are determined from results of in-situ physical monitoring measurements of one or more deposition rates used to deposit respective materials of the layers L(1), . . . , L(i) of the current instance of ICE(s). A third set of complex refractive indices $n^{*'}_{o-H}$, $n^{*'}_{o-L}$ and thicknesses $\{t'_o(1), \ldots, t'_o(j)\}$ of the layers L(1), . . . , L(j) of the current instance of ICE(s) are determined from results of in-situ optical monitoring measurements of change of intensity of probe-light transmitted through the layers L(1), . . . , L(i) of the current instance of ICE(s). A fourth set of complex refractive indices $n^{*'}_{s-H}$, $n^{*'}_{s}$-L and thicknesses $\{t'_s(1), \ldots, t'_s(j)\}$ of the layers L(1), . . . , L(j) of the ICEs are determined from results of in-situ spectroscopy measurements of probe-light spectrum modified by transmission through the layers L(1), . . . , L(i) of the current instance of ICE(s).

Values of complex refractive indices and thicknesses from the determined first, second, third and fourth sets are weighted to determine complex refractive indices $n^{*'}_H$, $n^{*'}_L$ and thicknesses {t'(1), t'(2), . . . , t'(i−1), t'(i)} of layers L(1), L(2), . . . , L(i−1), L(i) of the current instance of ICE(s). In this manner, the complex refractive indices and thicknesses can be determined in the following manner:

$$n^{*'}_H = W_e \cdot n^{*'}_{e-H} + W_o \cdot n^{*'}_{o-H} + W_s \cdot n^{*'}_{s-H}, \quad (1')$$

$$n^{*'}_L = W_e \cdot n^{*'}_{e-L} + W_o \cdot n^{*'}_{o-L} + W_s \cdot n^{*'}_{s-L}, \quad (2')$$

$$t'(i) = W_e \cdot t'_e(i) + W_p \cdot t'_p(i) + W_o \cdot t'_o(i) + W_s \cdot t'_s(i), \text{ where } i=1-N. \quad (3')$$

In equations (1'), (2') and (3'), a weight $W_e$ is used to weight results of the ellipsometry measurements, a weight $W_p$ is used to weight results of the physical monitoring measurements, a weight $W_o$ is used to weight results of the optical monitoring measurements, and a weight $W_s$ is used to weight results of the spectroscopy measurements. In some implementations, the weights of the four in-situ measurements are equal: $W_e=W_p=W_o=W_s=1/4$. In other implementations, the weights of the four in-situ measurements are proportional to an accuracy associated with each of the in-situ measurements as a function of the number of deposited layers $L(1), L(2), \ldots, L(i)$. For the first "j" layers when $i<j$, the weight $W_e$ used to weight the first set of complex refractive indices $n^{*'}_{e-H}, n^{*'}_{e-L}$ and thicknesses $\{t'_e(1), \ldots, t'_e(i)\}$ determined based on results of ellipsometry measurements is larger than each of the weights $W_p$, $W_o$ and $W_s$ associated with the second, third and fourth sets, respectively. For example, for the first two layers (j=2), the following weights may be used $W_e=0.8, W_p=0.1, W_o=0.05$ and $W_s=0.05$. For a stack with an intermediary number of layers when $j<i\le k$, the weight $W_p$ used to weight the second set of thicknesses $\{t'_p(1), \ldots, t'_p(i)\}$ determined based on results of physical monitoring measurements is larger than each of the weights $W_e$, $W_o$ and $W_s$ associated with the first, third and fourth sets, respectively. For example, for stacks having between 3-6 layers (j=2, k=6), the following weights may be used $W_p=0.7, W_e=0.1, W_o=0.1$ and $W_s=0.1$. For a stack with another larger intermediary number of layers when $k<i\le p$, the weight $W_o$ used to weight the third set of complex refractive indices $n^{*'}_{o-H}, n^{*'}_{o-L}$ and thicknesses $\{t'_o(1), \ldots, t'_o(i)\}$ determined based on results of optical monitoring measurements is larger than each of the weights $W_e$, $W_p$ and $W_s$ associated with the first, second and fourth sets, respectively. For example, for stacks having between 7-10 layers (k=6, p=10), the following weights may be used $W_o=0.6, W_e=0.1, W_p=0.1$ and $W_s=0.2$. For a stack with a larger number of layers when $p<i$, the weight $W_s$ used to weight the fourth set of complex refractive indices $n^{*'}_{s-H}, n^{*'}_{s-L}$ and thicknesses $\{t'_s(1), \ldots, t'_s(i)\}$ determined based on results of spectrometry measurements is larger than each of the weights $W_e$, $W_p$ and $W_o$ associated with the first, second and third sets, respectively. For example, for stacks having more than 10 layers (p=10), the following weights may be used $W_s=0.9, W_e=0.02, W_p=0.03$ and $W_o=0.05$.

In this example, the complex refractive indices $n^{*'}_H$ and $n^{*'}_L$ and thicknesses $t'(1), t'(2), \ldots, t'(i-1), t'(i)$ of the layers $L(1), L(2), \ldots, L(i-1)$ formed in previous iterations of the loop 415 and the layer $L(i)$ that is currently being formed are determined based on results of four in-situ measurements—ellipsometry, physical monitoring, optical monitoring and spectroscopy—performed during deposition of the layer $L(i)$.

In some implementations, the only in-situ measurements performed during deposition of the layer $L(i)$ are (1) in-situ physical monitoring to measure one or more deposition rates used to deposit respective materials of the ICE, (2) in-situ optical monitoring to measure change of intensity of the probe-light that interacted with the current instance of the ICE and (3) in-situ spectroscopy to measure a spectrum of the probe-light that interacted with the current instance of the ICE. Here, determining the complex refractive indices and thicknesses of the formed layers of the ICE includes weighting values of the measured one or more deposition rates, the measured change of intensity and the measured spectrum, such that the weights of the corresponding in-situ measurements are proportional to an accuracy associated with each of the in-situ measurements as a function of the number of deposited layers $L(1), L(2), \ldots, L(i)$. When fewer than a first number "j" of layers of the ICE have been formed ($i<j$), a weight $W_p$ of the one or more deposition rate values measured through physical monitoring is set to be larger than each of the weights $W_o$ of the change of intensity value measured through optical monitoring or $W_s$ of the spectrum measured through spectroscopy, $W_p>W_o, W_s$. When at least the first number "j" of layers but fewer that a second number "k" of layers of the ICE have been formed ($j\le i<k$), a weight $W_o$ of the change of intensity value measured through optical monitoring is set to be larger than each of the weights $W_p$ of the one or more deposition rate values measured through physical monitoring and $W_s$ of the spectrum measured through spectroscopy, $W_o>W_p, W_s$. And, when at least the second number "k" of layers have been formed ($k\le i$), a weight $W_s$ of the spectrum measured through spectroscopy is set to be larger than each of the weights $W_p$ of the one or more deposition rate values measured through physical monitoring and $W_o$ of the change of intensity value measured through optical monitoring $W_s>W_p, W_o$.

In other implementations, the only in-situ measurements performed during deposition of the layer $L(i)$ are (1) in-situ ellipsometry to measure amplitude and phase components of probe-light that interacted with the formed layers of the ICE, (2) physical monitoring to measure one or more deposition rates used to deposit respective materials of the ICE, and (3) in-situ spectroscopy to measure a spectrum of the probe-light that interacted with the current instance of the ICE. Here, determining the complex refractive indices and thicknesses of the formed layers of the ICE includes weighting values of the measured amplitude and phase components, the measured one or more deposition rates, and the measured spectrum, such that the weights of the corresponding in-situ measurements are proportional to an accuracy associated with each of the in-situ measurements as a function of the number of deposited layers $L(1), L(2), \ldots, L(i)$. When fewer than a first number "j" of layers of the ICE have been formed ($i<j$), a weight $W_o$ of the amplitude and phase component values measured through ellipsometry is set to be larger than each of the weights $W_p$ of the one or more deposition rate values measured through physical monitoring or $W_s$ of the spectrum measured through spectroscopy, $W_e>W_p, W_s$. When at least the first number "j" of layers but fewer that a second number "k" of layers of the ICE have been formed ($j\le i<k$), a weight $W_p$ of the one or more deposition rate values measured through physical monitoring is set to be larger than each of the weights $W_e$ of the amplitude and phase component values measured through ellipsometry or $W_s$ of the spectrum measured through spectroscopy, $W_p>W_e, W_s$. And, when at least the second number "k" of layers have been formed ($k\le i$), a weight $W_s$ of the spectrum measured through spectroscopy is set to be larger than each of the weights $W_e$ of the amplitude and phase component values measured through ellipsometry and $W_p$ of the one or more deposition rate values measured through physical monitoring, $W_s>W_e, W_p$.

In some other implementations, the only in-situ measurements performed during deposition of the layer $L(i)$ are (1) in-situ ellipsometry to measure amplitude and phase components of probe-light that interacted with the formed layers of the ICE, (2) physical monitoring to measure one or more deposition rates used to deposit respective materials of the ICE, and (3) in-situ optical monitoring to measure change of intensity of the probe-light that interacted with the current instance of the ICE. Here, determining the complex refractive indices and thicknesses of the formed layers of the ICE includes weighting values of the measured amplitude and phase components, the measured one or more deposition rates, and the measured change of intensity, such that the weights of the corresponding in-situ measurements are proportional to an accuracy associated with each of the in-situ measurements as a function of the number of deposited layers L(1), L(2), ..., L(i). When fewer than a first number "j" of layers of the ICE have been formed (i<j), a weight $W_o$ of the amplitude and phase component values measured through ellipsometry is set to be larger than each of the weights $W_p$ of the one or more deposition rate values measured through physical monitoring or $W_o$ of the change of intensity measured through optical monitoring, $W_e > W_p, W_o$. When at least the first number "j" of layers but fewer that a second number "k" of layers of the ICE have been formed (j≤i<k), a weight $W_p$ of the one or more deposition rate values measured through physical monitoring is set to be larger than each of the weights $W_e$ of the amplitude and phase component values measured through ellipsometry or $W_o$ of the change of intensity measured through optical monitoring, $W_p > W_e, W_o$. And, when at least the second number "k" of layers have been formed (k≤i), a weight $W_o$ of the change of intensity measured through optical monitoring is set to be larger than each of the weights $W_e$ of the amplitude and phase component values measured through ellipsometry and $W_p$ of the one or more deposition rate values measured through physical monitoring, $W_o > W_e, W_p$.

In the above examples, the complex refractive indices $n^{*\prime}_H$ and $n^{*\prime}_L$ and thicknesses t'(1), t'(2), ..., t'(i−1), t'(i) of the layers L(1), L(2), ..., L(i−1) formed in previous iterations of the loop 415 and the layer L(i) that is currently being formed are determined based on results of combinations of two in-situ optical measurements with in-situ physical monitoring performed during deposition of the layer L(i).

In some implementations, the only in-situ measurements performed during deposition of the layer L(i) are (1) in-situ ellipsometry to measure amplitude and phase components of the probe-light that interacted with the current instance of the ICE and (2) in-situ physical monitoring to measure one or more deposition rates used to deposit respective materials of the ICE. Here, determining the complex refractive indices and thicknesses of the formed layers of the ICE includes weighting values of the measured amplitude and phase components and the measured one or more deposition rates, such that the weights of the corresponding in-situ measurements are proportional to an accuracy associated with each of the in-situ measurements as a function of the number of deposited layers L(1), L(2), ..., L(i). When fewer than a first number "j" of layers of the ICE have been formed (i<j), a weight $W_e$ of the amplitude component and phase component values measured through ellipsometry is set to be larger than a weight $W_p$ of the one or more deposition rate values measured through physical monitoring, $W_e > W_p$. And, when at least the first number "j" of layers have been formed (j≤i), a weight $W_p$ of the one or more deposition rate values measured through physical monitoring is set to be equal to or larger than a weight $W_e$ of the amplitude component and phase component values measured through ellipsometry $W_e ≤ W_p$. In some cases, the weight $W_p$ of the one or more deposition rate values measured through physical monitoring is set to be larger than the weight $w_e$ of the amplitude component and phase component values measured through ellipsometry, $W_e < W_p$, when more than a second number "k" of layers have been formed (j<k<i).

In other implementations, the only in-situ measurements performed during deposition of the layer L(i) are (1) in-situ physical monitoring to measure one or more deposition rates used to deposit respective materials of the ICE and (2) in-situ optical monitoring to measure change of intensity of the probe-light that interacted with the formed layers of the ICE. Here, determining the complex refractive indices and thicknesses of the formed layers of the ICE includes weighting values of the measured one or more deposition rates and the measured change of intensity, such that the weights of the corresponding in-situ measurements are proportional to an accuracy associated with each of the in-situ measurements as a function of the number of deposited layers L(1), L(2), ..., L(i). When fewer than a first number "j" of layers of the ICE have been formed (i<j), a weight $W_p$ of the one or more deposition rate values measured through physical monitoring is set to be larger than a weight $W_o$ of the change of intensity value measured through optical monitoring, $W_p > W_o$. And, when at least the first number "j" of layers have been formed (j≤i), a weight $W_o$ of the change of intensity value measured through optical monitoring is set to be equal to or larger than a weight $W_p$ of the one or more deposition rate values measured through physical monitoring $W_p ≤ W_o$. In some cases, the weight $W_o$ of the change of intensity value measured through optical monitoring is set to be larger than the weight $W_p$ of the one or more deposition rate values measured through physical monitoring, $W_p < W_o$, when more than a second number "k" of layers have been formed (j<k<i).

In some other implementations, the only in-situ measurements performed during deposition of the layer L(i) are (1) in-situ physical monitoring to measure one or more deposition rates used to deposit respective materials of the ICE and (2) in-situ spectroscopy to measure a spectrum of the probe-light that interacted with the formed layers of the ICE. Here, determining the complex refractive indices and thicknesses of the formed layers of the ICE includes weighting values of the measured one or more deposition rates and the measured spectrum, such that the weights of the corresponding in-situ measurements are proportional to an accuracy associated with each of the in-situ measurements as a function of the number of deposited layers L(1), L(2), ..., L(i). When fewer than a first number "j" of layers of the ICE have been formed (i<j), a weight $W_p$ of the one or more deposition rate values measured through physical monitoring is set to be larger than a weight $W_s$ of the spectrum measured through spectroscopy, $W_p > W_s$. And, when at least the first number "j" of layers have been formed (j≤i), a weight $W_s$ of the spectrum measured through spectroscopy is set to be equal to or larger than the weight $W_p$ of the one or more deposition rate values measured through physical monitoring $W_p ≤ W_s$. In some cases, the weight $W_s$ of the spectrum measured through spectroscopy is set to be larger than the weight $W_p$ of the one or more deposition rate values measured through physical monitoring, $W_p < W_s$, when more than a second number "k" of layers have been formed (j<k<i).

At 450, deposition of current and subsequent layers L(i), L(i+1), ... of the ICE(s) is adjusted, if necessary, based on determined complex refractive indices $n^{*\prime}_H, n^{*\prime}_L$ and thicknesses {t'(1), t'(2), ..., t'(i−1), t'(i)} of deposited layers L(1), L(2), ..., L(i−1) and the layer L(i) currently being deposited. For example, a deposition rate used to form the layer L(i) currently being formed and other layers L(i+1), L(i+2), ... remaining to be formed can be adjusted based on a comparison between values of the complex refractive indices and thicknesses of the layers of the current instance of the ICEs and their respective target values. Alternatively or additionally, complex refractive indices corresponding to the layer L(i) being current formed and other layers L(i+1), L(i+2), ... remaining to be formed can be adjusted based on a comparison between values of the complex refractive indices and thicknesses of the layers of the current instance of the ICEs and their respective target values.

Further, in order to determine whether target thicknesses of the layer L(i) being current formed and other layers L(i+1), L(i+2), ..., L(N) remaining to be formed should be updated, the following verification is performed. An SEC(i) of the ICE is predicted to represent the ICE's performance if the ICE were completed to have the formed layers L(1), L(2), ..., L(i−1) with the determined thicknesses t'(1), t'(2), ..., t'(i−1), and the layer L(i) currently being formed and other layers L(i+1), L(i+2), ..., L(N) remaining to be formed with target thicknesses t(i), t(i), ..., t(N). Here, the predicted SEC(i) is caused by deviations of the determined complex refractive indices and thicknesses of the formed layers from their respective complex refractive indices and target thicknesses specified by the current ICE design. If the predicted SEC(i) does not exceed the maximum allowed $SEC_{max}$, $SEC(i) \leq SEC_{max}$, then the forming of the current layer L(i) is completed in accordance to its target thickness t(i) and a next iteration of the loop 415 will be triggered to form the next layer L(i+1) to its target thickness t(i+1).

If, however, the predicted SEC(i;N) exceeds the maximum allowed $SEC_{max}$, $SEC(i;N) > SEC_{max}$, then target thicknesses of the layer L(i) currently being formed and other layers L(i+1), L(i+2), ..., L(N) remaining to be formed are modified based on the determined complex refractive indices and thicknesses of the formed layers L(1), L(2), ..., L(i). This optimization may change the total number of layers of the ICE from the specified total number N of layers to a new total number N' of layers, but constrains the thicknesses of the layers L(1), L(2), ..., L(i) (of the current instance of the ICE) to the determined thicknesses t'(1), t'(2), ..., t'(i). In this manner, the optimization obtains, in analogy with the process 200 described above in connection with FIG. 2, new target thicknesses t"(i), t"(i+1), ..., t"(N') of the layer L(i) currently being formed and other layers L(i+1), ..., L(N') remaining to be formed, such that a new target $SEC'_t(i;N')$ of the ICE—for the ICE having the first layers L(1), L(2), ..., L(i−1) formed with the determined thicknesses t'(1), t'(2), ..., t'(i−1), and the layer L(i) currently being formed and other layers L(i+1), ..., L(N') remaining to be formed with the new target thicknesses t"(i), t"(i+1), ..., t"(N')—is minimum and does not exceed the maximum allowed $SEC_{max}$, $SEC'_t(i;N') \leq SEC_{max}$.

Once the previous instance of the ICE design is updated with specification of the new total number of layers N' and the new target thicknesses t"(i), t"(i+1), ..., t"(N')—which are used to form the current layer L(i) and the remaining layers L(i+1), ..., L(N') and correspond to the new target $SEC'_t(i; N')$—the forming of the current layer L(i) is completed in accordance with its new target thickness t"(i) and a next iteration of the loop 415 will be triggered to form the next layer L(i+1) from the new total number of layers N' to its new target thickness t"(i+1). In this manner, the remaining layers of the ICE will be formed based on the updated ICE design, at least until another update is performed.

Some embodiments have been described in detail above, and various modifications are possible. While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Other embodiments fall within the scope of the following claims.

What is claimed is:

1. A method comprising:
   receiving, by a fabrication system, a design of an integrated computational element (ICE), the ICE design comprising specification of a substrate and a plurality of layers, their respective target thicknesses and complex refractive indices, wherein complex refractive indices of adjacent layers are different from each other, and wherein a notional ICE fabricated in accordance with the ICE design is related to a characteristic of a sample;
   forming, by the fabrication system, at least some of the plurality of layers of the ICE in accordance with the ICE design;
   performing, by a measurement system associated with the fabrication system, at least two different types of in-situ measurements, wherein a first type of in-situ measurement from among the at least two different types of in-situ measurements is performed when fewer than a first number of layers of the ICE have been formed, and a second type of in-situ measurement from among the at least two different types of in-situ measurements is performed when at least the first number of layers of the ICE have been formed;
   predicting, by the fabrication system using results of the at least two different types of in situ measurements, performance of the ICE relative to the ICE design; and
   adjusting, by the fabrication system, said forming of the layers remaining to be formed, at least in part, by updating the ICE design based on the predicted performance.

2. The method of claim 1, wherein said performing the at least two different types of in-situ measurements comprises
   performing in-situ ellipsometry when fewer than the first number of layers of the ICE have been formed to measure amplitude and phase components of probe-light that interacted with the formed layers of the ICE, and
   performing in-situ spectroscopy when at least the first number of layers has been formed to measure a spectrum of probe-light that interacted with the formed layers of the ICE.

3. The method of claim 1, wherein said performing the at least two different types of in-situ measurements comprises
   performing in-situ optical monitoring when fewer than the first number of layers of the ICE have been formed to measure change of intensity of probe-light that interacted with the formed layers of the ICE, and
   performing in-situ spectroscopy when at least the first number of layers has been formed to measure a spectrum of probe-light that interacted with the formed layers of the ICE.

4. The method of claim 1, wherein said performing the at least two different types of in-situ measurements comprises
   performing in-situ ellipsometry when fewer than the first number of layers of the ICE have been formed to measure amplitude and phase components of probe-light that interacted with the formed layers of the ICE, and performing in-situ optical monitoring when at least the first number of layers has been formed to measure change of intensity of probe-light that interacted with the formed layers of the ICE.

5. The method of claim 1, wherein said performing the at least two different types of in-situ measurements comprises performing in-situ ellipsometry when fewer than the first number of layers of the ICE have been formed to measure amplitude and phase components of probe-light that interacted with the formed layers of the ICE, performing in-situ optical monitoring when at least the first number of layers but fewer than a second number of layers of the ICE have been formed to measure change of intensity of probe-light that interacted with the formed layers of the ICE, and performing in-situ spectroscopy when at least the second number of layers has been formed to measure a spectrum of probe-light that interacted with the formed layers of the ICE.

6. The method of claim 5, further comprising performing, when at least the first number of layers but fewer that a second number of layers of the ICE have been formed and in addition to the in-situ optical monitoring, in-situ ellipsometry to measure the amplitude and phase components and spectroscopy to measure the spectrum.

7. The method of claim 6, further comprising performing, for each of at least some of the layers of the ICE, in-situ optical monitoring to measure the change of intensity in addition to the in-situ ellipsometry when fewer than the first number of layers of the ICE have been formed; and the in-situ spectroscopy when at least the second number of layers has been formed.

8. The method of claim 1, wherein said adjusting comprises updating a deposition rate used to form the layers remaining to be formed based on the determined complex refractive indices and thicknesses of the formed layers of the ICE.

9. The method of claim 1, wherein said adjusting comprises modifying complex refractive indices of the layers remaining to be formed based on the determined complex refractive indices and thicknesses of the formed layers of the ICE.

10. The method of claim 1, wherein said adjusting comprises modifying target thicknesses of the layers remaining to be formed based on the determined complex refractive indices and thicknesses of the formed layers of the ICE.

11. The method of claim 10, wherein said adjusting comprises changing a total number of layers specified by the ICE design to a new total number of layers.

12. The method of claim 1, wherein said performing the at least two different types of in-situ measurements comprises performing in-situ ellipsometry when fewer than the first number of layers of the ICE have been formed to measure amplitude and phase components of probe-light that interacted with the formed layers of the ICE, and performing in-situ physical monitoring when at least the first number of layers has been formed to measure one or more deposition rates used to deposit respective materials of the formed layers of the ICE.

13. The method of claim 1, wherein said performing the at least two different types of in-situ measurements comprises performing in-situ physical monitoring when fewer than the first number of layers of the ICE have been formed to measure one or more deposition rates used to deposit respective materials of the formed layers of the ICE, and performing in-situ optical monitoring when at least the first number of layers has been formed to measure change of intensity of probe-light that interacted with the formed layers of the ICE.

14. The method of claim 1, wherein said performing the at least two different types of in-situ measurements comprises performing in-situ physical monitoring when fewer than the first number of layers of the ICE have been formed to measure one or more deposition rates used to deposit respective materials of the formed layers of the ICE, and performing in-situ spectroscopy when at least the first number of layers has been formed to measure a spectrum of probe-light that interacted with the formed layers of the ICE.

15. The method of claim 1, wherein said performing the at least two different types of in-situ measurements comprises performing in-situ physical monitoring when fewer than the first number of layers of the ICE have been formed to measure one or more deposition rates used to deposit respective materials of the formed layers of the ICE, performing in-situ optical monitoring when at least the first number of layers but fewer than a second number of layers of the ICE have been formed to measure change of intensity of probe-light that interacted with the formed layers of the ICE, and performing in-situ spectroscopy when at least the second number of layers has been formed to measure a spectrum of probe-light that interacted with the formed layers of the ICE.

16. The method of claim 15, further comprising performing, when at least the first number of layers but fewer that a second number of layers of the ICE have been formed and in addition to the in-situ optical monitoring, in-situ physical monitoring to measure the one or more deposition rates and spectroscopy to measure the spectrum.

17. The method of claim 16, further comprising performing, for each of at least some of the layers of the ICE, in-situ optical monitoring to measure the change of intensity in addition to the in-situ physical monitoring when fewer than the first number of layers of the ICE have been formed; and the in-situ spectroscopy when at least the second number of layers has been formed.

18. The method of claim 1, wherein said performing the at least two different types of in-situ measurements comprises performing in-situ ellipsometry when fewer than the first number of layers of the ICE have been formed to measure amplitude and phase components of probe-light that interacted with the formed layers of the ICE, performing in-situ physical monitoring when at least the first number of layers but fewer than a second number of layers of the ICE have been formed to measure one or more deposition rates used to deposit respective materials of the formed layers of the ICE, and performing in-situ spectroscopy when at least the second number of layers has been formed to measure a spectrum of probe-light that interacted with the formed layers of the ICE.

19. The method of claim 18, further comprising performing, when at least the first number of layers but fewer that a second number of layers of the ICE have been formed and in addition to the in-situ physical monitoring, in-situ ellipsometry to measure the amplitude and phase components and spectroscopy to measure the spectrum.

20. The method of claim 19, further comprising performing, for each of at least some of the layers of the ICE, in-situ physical monitoring to measure the one or more deposition rates in addition to the in-situ ellipsometry when fewer than the first number of layers of the ICE have been formed; and the in-situ spectroscopy when at least the second number of layers has been formed.

21. The method of claim 1, wherein said performing the at least two different types of in-situ measurements comprises performing in-situ ellipsometry when fewer than the first number of layers of the ICE have been formed to measure amplitude and phase components of probe-light that interacted with the formed layers of the ICE, performing in-situ physical monitoring when at least the first number of layers but fewer than a second number of layers of the ICE have been formed to measure one or more deposition rates used to deposit respective materials of the formed layers of the ICE, and performing in-situ optical monitoring when at least the second number of layers has been formed to measure change of intensity of probe-light that interacted with the formed layers of the ICE.

22. The method of claim 21, further comprising performing, when at least the first number of layers but fewer that a second number of layers of the ICE have been formed and in addition to the in-situ physical monitoring, in-situ ellipsometry to measure the amplitude and phase components and spectroscopy to measure a spectrum.

23. The method of claim 22, further comprising performing, for each of at least some of the layers of the ICE, in-situ physical monitoring to measure the one or more deposition rates in addition to the in-situ ellipsometry when fewer than the first number of layers of the ICE have been formed; and the in-situ optical monitoring when at least the second number of layers has been formed.

24. The method of claim 1, wherein said performing the at least two different types of in-situ measurements comprises performing in-situ ellipsometry when fewer than the first number of layers of the ICE have been formed to measure amplitude and phase components of probe-light that interacted with the formed layers of the ICE, performing in-situ physical monitoring when at least the first number of layers but fewer than a second number of layers of the ICE have been formed to measure one or more deposition rates used to deposit respective materials of the formed layers of the ICE, performing in-situ optical monitoring when at least the second number of layers but fewer than a third number of layer of the ICE have been formed to measure change of intensity of probe-light that interacted with the formed layers of the ICE, and performing in-situ spectroscopy when at least the third number of layers has been formed to measure a spectrum of probe-light that interacted with the formed layers of the ICE.

25. A method comprising:

receiving, by a fabrication system, a design of an integrated computational element (ICE) design, the ICE design comprising specification of a substrate and a plurality of layers, their respective target thicknesses and complex refractive indices, wherein complex refractive indices of adjacent layers are different from each other, and wherein a notional ICE fabricated in accordance with the ICE design is related to a characteristic of a sample;

forming, by the fabrication system, at least some of the plurality of layers of the ICEs in accordance with the ICE design;

performing, by a measurement system associated with the fabrication system, at least two different types of in-situ measurements for each of at least some of the layers of the ICE;

determining, by the fabrication system, complex refractive indices and thicknesses of the formed layers of the ICE by weighting results of the at least two different types of in situ measurements, wherein when fewer than a first number of layers of the ICE have been formed, a first weight used for weighting a result of a first type of in-situ measurement from among the at least two different types of in-situ measurements is larger than a second weight used for weighting a result of a second type of in-situ measurement from among the at least two different types of in-situ measurements, and when at least the first number of layers of the ICE have been formed, the first weight used for weighting the result of the first type of in-situ measurement is equal to or smaller than the second weight used for weighting the result of the second type of in-situ measurement; and adjusting, by the fabrication system, said forming of the layers remaining to be formed, at least in part, by updating the ICE design based on the determined complex refractive indices and thicknesses of the formed layers of the ICE.

26. The method of claim 25, wherein the at least two different types of in-situ measurements are performed for each of at least some of the layers of the ICE and comprise in-situ ellipsometry to measure amplitude and phase components of probe-light that interacted with the formed layers of the ICE, and in-situ spectroscopy to measure a spectrum of probe-light that interacted with the formed layers of the ICE.

27. The method of claim 26, wherein said weighting comprises when fewer than the first number of layers of the ICE have been formed, setting a weight of the amplitude component and phase component values measured through ellipsometry to be larger than a weight of the spectrum measured through spectroscopy, and when at least the first number of layers has been formed, setting a weight of the spectrum measured through spectroscopy to be equal to or larger than the weight of the amplitude component and phase component values measured through ellipsometry.

28. The method of claim 27, wherein the weight of the spectrum measured through spectroscopy is set to be larger than the weight of the amplitude component and phase component values measured through ellipsometry when more than a second number of layers have been formed, such that the second number of layers is larger than the first number of layers.

29. The method of claim 25, wherein the at least two different types of in-situ measurements are performed for each of at least some of the layers of the ICE and comprise in-situ ellipsometry to measure amplitude and phase components of probe-light that interacted with the formed layers of the ICE, and in-situ optical monitoring to measure change of intensity of probe-light that interacted with the formed layers of the ICE.

30. The method of claim 29, wherein said weighting comprises when fewer than the first number of layers of the ICE have been formed, setting a weight of the amplitude component and phase component values measured through ellipsometry to be larger than a weight of the change of intensity value measured through optical monitoring, and when at least the first number of layers have been formed, setting a weight of the change of intensity value measured through optical monitoring to be equal to or larger than the weight of the amplitude component and phase component values measured through ellipsometry.

31. The method of claim 30, wherein the weight of the change of intensity value measured through optical monitoring is set to be larger than the weight of the amplitude component and phase component values measured through ellipsometry when more than a second number of layers have been formed, such that the second number of layers is larger than the first number of layers.

32. The method of claim 25, wherein the at least two different types of in-situ measurements are performed for each of at least some of the layers of the ICE and comprise in-situ optical monitoring to measure change of intensity of probe-light that interacted with the formed layers of the ICE, and in-situ spectroscopy to measure a spectrum of probe-light that interacted with the formed layers of the ICE.

33. The method of claim 32, wherein said weighting comprises when fewer than the first number of layers of the ICE have been formed, setting a weight of the change of intensity value measured through optical monitoring to be larger than a weight of the spectrum measured through spectroscopy, and when at least the first number of layers have been formed, setting a weight of the spectrum measured through spectroscopy to be equal to or larger than the weight of the change of intensity value measured through optical monitoring.

34. The method of claim 33, wherein the weight of the spectrum is set to be larger than the weight of the change of intensity value measured through optical monitoring when more than a second number of layers have been formed, such that the second number of layers is larger than the first number of layers.

35. The method of claim 25, wherein the at least two different types of in-situ measurements are performed for each of at least some of the layers of the ICE and comprise in-situ ellipsometry to measure amplitude and phase components of probe-light that interacted with the formed layers of the ICE, in-situ optical monitoring to measure change of intensity of probe-light that interacted with the formed layers of the ICE, and in-situ spectroscopy to measure a spectrum of probe-light that interacted with the formed layers of the ICE.

36. The method of claim 35, wherein said weighting comprises when fewer than the first number of layers of the ICE have been formed, setting a weight of the amplitude component and phase component values measured through ellipsometry to be larger than each of weights of the change of intensity value measured through optical monitoring and the spectrum measured through spectroscopy, when at least the first number of layers but fewer than a second number of layers of the ICE have been formed, setting the weight of the change of intensity value measured through optical monitoring to be larger than each of the weights of the amplitude component and phase component values measured through ellipsometry and the spectrum measured through spectroscopy, and when at least the second number of layers has been formed, setting the weight of the spectrum measured through spectroscopy to be larger than each of the weights of the amplitude component and phase component values measured through ellipsometry and the change of intensity value measured through optical monitoring.

37. The method of claim 36, wherein the weight of the spectrum measured through spectroscopy is set to be equal with the weight of the amplitude component and phase component values measured through ellipsometry when at least the first number of layers but fewer than the second number of layers has been formed.

38. The method of claim 36, wherein the weight of the change of intensity value measured through optical monitoring is set to be larger than the weight of the amplitude component and phase component values measured through ellipsometry when fewer than the first number of layers of the ICE have been formed, and the weight of the spectrum measured through spectroscopy when at least the second number of layers of the ICE has been formed.

39. The method of claim 25, wherein the at least two different types of in-situ measurements are performed for each of at least some of the layers of the ICE and comprise in-situ ellipsometry to measure amplitude and phase components of probe-light that interacted with the formed layers of the ICE, and in-situ physical monitoring to measure one or more deposition rates used to deposit respective materials of the formed layers of the ICE.

40. The method of claim 39, wherein said weighting comprises when fewer than the first number of layers of the ICE have been formed, setting a weight of the amplitude component and phase component values measured through ellipsometry to be larger than a weight of the one or more deposition rate values measured through physical monitoring, and when at least the first number of layers have been formed, setting the weight of the one or more deposition rate values measured through physical monitoring to be equal to or larger than the weight of the amplitude component and phase component values measured through ellipsometry.

41. The method of claim 40, wherein the weight of the one or more deposition rate values measured through physical monitoring is set to be larger than the weight of the amplitude component and phase component values measured through ellipsometry when more than a second number of layers have been formed, such that the second number of layers is larger than the first number of layers.

42. The method of claim 25, wherein the at least two different types of in-situ measurements are performed for each of at least some of the layers of the ICE and comprise in-situ physical monitoring to measure one or more deposition rates used to deposit respective materials of the formed layers of the ICE, and in-situ optical monitoring to measure change of intensity of probe-light that interacted with the formed layers of the ICE.

43. The method of claim 42, wherein said weighting comprises
when fewer than the first number of layers of the ICE have been formed, setting a weight of the one or more deposition rate values measured through physical monitoring to be larger than a weight of the change of intensity value measured through optical monitoring, and
when at least the first number of layers have been formed, setting the weight of the change of intensity value measured through optical monitoring to be equal to or larger than the weight of the one or more deposition rate values measured through physical monitoring.

44. The method of claim 43, wherein the weight of the change of intensity value measured through optical monitoring is set to be larger than the weight of the one or more deposition rate values measured through optical monitoring when more than a second number of layers have been formed, such that the second number of layers is larger than the first number of layers.

45. The method of claim 25, wherein the at least two different types of in-situ measurements are performed for each of at least some of the layers of the ICE and comprise
in-situ physical monitoring to measure one or more deposition rates used to deposit respective materials of the formed layers of the ICE, and
in-situ spectroscopy to measure a spectrum of probe-light that interacted with the formed layers of the ICE.

46. The method of claim 45, wherein said weighting comprises
when fewer that the first number of layers of the ICE have been formed, setting a weight of the one or more deposition rate values measured through physical monitoring to be larger than a weight of the spectrum measured through spectroscopy, and
when at least the first number of layers have been formed, setting the weight of the spectrum measured through spectroscopy to be equal to or larger than the weight of the one or more deposition rate values measured through physical monitoring.

47. The method of claim 46, wherein the weight of the spectrum is set to be larger than the weight of the one or more deposition rate values measured through physical monitoring when more than a second number of layers have been formed, such that the second number of layers is larger than the first number of layers.

48. The method of claim 25, wherein the at least two different types of in-situ measurements are performed for each of at least some of the layers of the ICE and comprise
in-situ ellipsometry to measure amplitude and phase components of probe-light that interacted with the formed layers of the ICE,
in-situ physical monitoring to measure one or more deposition rates used to deposit respective materials of the formed layers of the ICE, and
in-situ spectroscopy to measure a spectrum of probe-light that interacted with the formed layers of the ICE.

49. The method of claim 48, wherein said weighting comprises
when fewer than the first number of layers of the ICE have been formed, setting a weight of the amplitude component and phase component values measured through ellipsometry to be larger than each of weights of the one or more deposition rate values measured through physical monitoring and the spectrum measured through spectroscopy,
when at least the first number of layers but fewer that a second number of layers of the ICE have been formed, setting the weight of the one or more deposition rate values measured through physical monitoring to be larger than each of the weights of the amplitude component and phase component values measured through ellipsometry and the spectrum measured through spectroscopy, and
when at least the second number of layers has been formed, setting the weight of the spectrum measured through spectroscopy to be larger than each of the weights of the amplitude component and phase component values measured through ellipsometry and the one or more deposition rate values measured through physical monitoring.

50. The method of claim 49, wherein the weight of the spectrum measured through spectroscopy is set to be equal with the weight of the amplitude component and phase component values measured through ellipsometry when at least the first number of layers but fewer than the second number of layers has been formed has been formed.

51. The method of claim 49, wherein the weight of the one or more deposition rate values measured through physical monitoring is set to be larger than
the weight of the amplitude component and phase component values measured through ellipsometry when fewer than the first number of layers of the ICE have been formed, and
the weight of the spectrum measured through spectroscopy when at least the second number of layers of the ICE has been formed.

52. The method of claim 25, wherein the at least two different types of in-situ measurements are performed for each of at least some of the layers of the ICE and comprise
in-situ ellipsometry to measure amplitude and phase components of probe-light that interacted with the formed layers of the ICE,
in-situ physical monitoring to measure one or more deposition rates used to deposit respective materials of the formed layers of the ICE, and
in-situ optical monitoring to measure change of intensity of probe-light that interacted with the formed layers of the ICE.

53. The method of claim 52, wherein said weighting comprises
when fewer than the first number of layers of the ICE have been formed, setting a weight of the amplitude component and phase component values measured through ellipsometry to be larger than each of weights of the one or more deposition rate values measured through physical monitoring and the change of intensity measured through optical monitoring,
when at least the first number of layers but fewer that a second number of layers of the ICE have been formed, setting the weight of the one or more deposition rate values measured through physical monitoring to be larger than each of the weights of the amplitude component and phase component values measured through ellipsometry and the change of intensity measured through optical monitoring, and
when at least the second number of layers has been formed, setting the weight of the change of intensity measured through optical monitoring to be larger than each of the weights of the amplitude component and phase component values measured through ellipsometry and the one or more deposition rate values measured through physical monitoring.

54. The method of claim 53, wherein the weight of the change of intensity measured through optical monitoring is set to be equal with the weight of the amplitude component and phase component values measured through ellipsometry when at least the first number of layers but fewer than the second number of layers have been formed has been formed.

55. The method of claim 53, wherein the weight of the one or more deposition rate values measured through physical monitoring is set to be larger than
the weight of the amplitude component and phase component values measured through ellipsometry when fewer than the first number of layers of the ICE have been formed has been formed and,
the weight of the change of intensity measured through optical monitoring when at least the second number of layers of the ICE has been formed.

56. The method of claim 25, wherein the at least two different types of in-situ measurements are performed for each of at least some of the layers of the ICE and comprise
in-situ physical monitoring to measure one or more deposition rates used to deposit respective materials of the formed layers of the ICE,
in-situ optical monitoring to measure change of intensity of probe-light that interacted with the formed layers of the ICE, and
in-situ spectroscopy to measure a spectrum of probe-light that interacted with the formed layers of the ICE.

57. The method of claim 56, wherein said weighting comprises
when fewer than the first number of layers of the ICE have been formed, setting a weight of the one or more deposition rate values measured through physical monitoring to be larger than each of weights of the change of intensity value measured through optical monitoring and the spectrum measured through spectroscopy,
when at least the first number of layers but fewer that a second number of layers of the ICE have been formed, setting the weight of the change of intensity value measured through optical monitoring to be larger than each of the weights of the one or more deposition rate values measured through physical monitoring and the spectrum measured through spectroscopy, and
when at least the second number of layers has been formed, setting the weight of the spectrum measured through spectroscopy to be larger than each of the weights of the one or more deposition rate values measured through physical monitoring and the change of intensity value measured through optical monitoring.

58. The method of claim 57, wherein the weight of the spectrum measured through spectroscopy is set to be equal with the weight of the one or more deposition rate values measured through physical monitoring when at least the first number of layers but fewer than the second number of layers has been formed has been formed.

59. The method of claim 57, wherein the weight of the change of intensity value measured through optical monitoring is set to be larger than
the weight of the one or more deposition rate values measured through physical monitoring when fewer than the first number of layers of the ICE have been formed has been formed and,
the weight of the spectrum measured through spectroscopy when at least the second number of layers of the ICE has been formed.

60. The method of claim 25, wherein the at least two different types of in-situ measurements are performed for each of at least some of the layers of the ICE and comprise
in-situ ellipsometry to measure amplitude and phase components of probe-light that interacted with the formed layers of the ICE,
in-situ physical monitoring to measure one or more deposition rates used to deposit respective materials of the formed layers of the ICE,
in-situ optical monitoring to measure change of intensity of probe-light that interacted with the formed layers of the ICE, and
in-situ spectroscopy to measure a spectrum of probe-light that interacted with the formed layers of the ICE.

61. The method of claim 60, wherein said weighting comprises
when fewer than the first number of layers of the ICE have been formed, setting a weight of the amplitude component and phase component values measured through ellipsometry to be larger than each of weights of the one or more deposition rate values measured through physical monitoring, the change of intensity value measured through optical monitoring and the spectrum measured through spectroscopy,
when at least the first number of layers but fewer than a second number of layers of the ICE have been formed, setting the weight of the one or more deposition rate values measured through physical monitoring to be larger than each of the weights of the amplitude component and phase component values measured through ellipsometry, the change of intensity value measured through optical monitoring, and the spectrum measured through spectroscopy,
when at least the second number of layers but fewer than a third number of layers of the ICE have been formed, setting the weight of the change of intensity value measured through optical monitoring to be larger than each of the weights of the amplitude component and phase component values measured through ellipsometry, the one or more deposition rate values measured through physical monitoring, and the spectrum measured through spectroscopy, and
when at least the third number of layers has been formed, setting the weight of the spectrum measured through spectroscopy to be larger than each of the weights of the amplitude component and phase component values measured through ellipsometry, the one or more deposition rate values measured through physical monitoring, and the change of intensity value measured through optical monitoring.

* * * * *